United States Patent
Li

(10) Patent No.: US 8,244,348 B2
(45) Date of Patent: Aug. 14, 2012

(54) METHOD AND APPARATUS FOR CARDIAC ARRHYTHMIA CLASSIFICATION USING TEMPLATE BAND-BASED MORPHOLOGY ANALYSIS

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 826 days.

(21) Appl. No.: 12/206,198

(22) Filed: Sep. 8, 2008

(65) Prior Publication Data
US 2009/0005826 A1 Jan. 1, 2009

Related U.S. Application Data

(63) Continuation of application No. 11/038,996, filed on Jan. 20, 2005, now Pat. No. 7,430,446.

(51) Int. Cl.
*A61N 1/39* (2006.01)

(52) U.S. Cl. .......... 607/5; 607/1; 607/2; 607/9; 607/14; 607/115

(58) Field of Classification Search .............. None
See application file for complete search history.

(56) References Cited

U.S. PATENT DOCUMENTS

| | | | |
|---|---|---|---|
| 4,023,564 A | 5/1977 | Valiquette et al. |
| 4,529,401 A | 7/1985 | Leslie et al. |
| 4,531,527 A | 7/1985 | Reinhold, Jr. et al. |
| 4,583,553 A | 4/1986 | Shah et al. |
| 4,589,420 A | 5/1986 | Adams et al. |
| 4,721,114 A | 1/1988 | DuFault et al. |
| 4,802,491 A | 2/1989 | Cohen et al. |
| 4,884,345 A | 12/1989 | Long |
| 4,924,875 A | 5/1990 | Chamoun |
| 4,947,857 A | 8/1990 | Albert et al. |
| 5,000,189 A | 3/1991 | Throne et al. |
| 5,014,284 A | 5/1991 | Langer et al. |
| 5,014,698 A | 5/1991 | Cohen |
| 5,020,540 A | 6/1991 | Chamoun |
| 5,107,850 A | 4/1992 | Olive |
| 5,109,842 A | 5/1992 | Adinolfi |
| 5,139,028 A | 8/1992 | Steinhaus et al. |
| 5,156,148 A | 10/1992 | Cohen |

(Continued)

FOREIGN PATENT DOCUMENTS

DE 4405827 A1 6/1995

(Continued)

OTHER PUBLICATIONS

Cazares, S., et al., "Arrhythmia Discrimination Based on Determination of Rate Dependency", U.S. Appl. No. 11/312,280, filed Dec. 20, 2005, 41 pgs.

(Continued)

*Primary Examiner* — Carl H Layno
*Assistant Examiner* — Deborah Malamud
(74) *Attorney, Agent, or Firm* — Schwegman, Lundberg & Woessner, P.A.

(57) ABSTRACT

An implantable cardioverter/defibrillator (ICD) includes a tachyarrhythmia detection and classification system that classifies tachyarrhythmias based on a morphological analysis of arrhythmic waveforms and a template waveform. Correlation coefficients each computed between morphological features of an arrhythmic waveform and morphological features of the template waveform provide for the basis for classifying the tachyarrhythmia. In one embodiment, a correlation analysis takes into account the uncertainty associated with the production of the template waveform by using a template band that includes confidence intervals.

20 Claims, 25 Drawing Sheets

U.S. PATENT DOCUMENTS

| | | | |
|---|---|---|---|
| 5,184,615 A | 2/1993 | Nappholz et al. |
| 5,193,550 A | 3/1993 | Duffin |
| 5,215,098 A | 6/1993 | Steinhaus et al. |
| 5,217,021 A | 6/1993 | Steinhaus et al. |
| 5,240,009 A | 8/1993 | Williams |
| 5,247,021 A | 9/1993 | Fujisawa et al. |
| 5,255,186 A | 10/1993 | Steinhaus et al. |
| 5,269,301 A | 12/1993 | Cohen |
| 5,271,411 A | 12/1993 | Ripley et al. |
| 5,273,049 A | 12/1993 | Steinhaus et al. |
| 5,275,621 A | 1/1994 | Mehra |
| 5,277,190 A | 1/1994 | Moulton |
| 5,280,792 A | 1/1994 | Leong et al. |
| 5,292,348 A | 3/1994 | Saumarez et al. |
| 5,311,874 A | 5/1994 | Baumann et al. |
| 5,312,445 A | 5/1994 | Nappholz et al. |
| 5,313,953 A | 5/1994 | Yomtov et al. |
| 5,330,504 A | 7/1994 | Somerville et al. |
| 5,331,966 A | 7/1994 | Bennett et al. |
| 5,350,406 A | 9/1994 | Nitzsche et al. |
| 5,360,436 A | 11/1994 | Alt et al. |
| 5,366,487 A | 11/1994 | Adams et al. |
| 5,388,578 A | 2/1995 | Yomtov et al. |
| 5,400,795 A | 3/1995 | Murphy et al. |
| 5,404,880 A | 4/1995 | Throne |
| 5,411,031 A | 5/1995 | Yomtov |
| 5,421,830 A | 6/1995 | Epstein et al. |
| 5,447,519 A | 9/1995 | Peterson |
| 5,447,524 A | 9/1995 | Alt |
| 5,456,261 A | 10/1995 | Luczyk |
| 5,458,623 A | 10/1995 | Lu et al. |
| 5,478,807 A | 12/1995 | Cronin et al. |
| 5,509,927 A | 4/1996 | Epstein et al. |
| 5,520,191 A | 5/1996 | Karlsson et al. |
| 5,542,430 A | 8/1996 | Farrugia et al. |
| 5,622,178 A | 4/1997 | Gilham |
| 5,634,468 A | 6/1997 | Platt et al. |
| 5,645,070 A | 7/1997 | Turcott |
| 5,676,687 A | 10/1997 | Ayers |
| 5,682,900 A | 11/1997 | Arand et al. |
| 5,683,425 A | 11/1997 | Hauptmann |
| 5,687,737 A | 11/1997 | Branham et al. |
| 5,712,801 A | 1/1998 | Turcott |
| 5,713,367 A | 2/1998 | Arnold et al. |
| 5,724,985 A | 3/1998 | Snell et al. |
| 5,730,142 A | 3/1998 | Sun et al. |
| 5,738,105 A | 4/1998 | Kroll |
| 5,755,739 A | 5/1998 | Sun et al. |
| 5,759,158 A | 6/1998 | Swanson |
| 5,772,604 A | 6/1998 | Langberg et al. |
| 5,778,881 A | 7/1998 | Sun et al. |
| 5,779,645 A | 7/1998 | Olson et al. |
| 5,782,888 A | 7/1998 | Sun et al. |
| 5,792,065 A | 8/1998 | Xue et al. |
| 5,795,303 A | 8/1998 | Swanson et al. |
| 5,797,399 A | 8/1998 | Morris et al. |
| 5,797,849 A | 8/1998 | Vesely et al. |
| 5,817,133 A | 10/1998 | Houben |
| 5,819,007 A | 10/1998 | Elghazzawi |
| 5,819,741 A | 10/1998 | Karlsson et al. |
| 5,827,197 A | 10/1998 | Bocek et al. |
| 5,848,972 A | 12/1998 | Triedman et al. |
| 5,857,977 A | 1/1999 | Caswell et al. |
| 5,858,977 A | 1/1999 | Aukerman et al. |
| 6,016,442 A | 1/2000 | Hsu et al. |
| 6,179,865 B1 | 1/2001 | Hsu et al. |
| 6,192,273 B1 | 2/2001 | Igel et al. |
| 6,266,554 B1 | 7/2001 | Hsu et al. |
| 6,275,732 B1 | 8/2001 | Hsu et al. |
| 6,434,417 B1 | 8/2002 | Lovett |
| 6,456,871 B1 | 9/2002 | Hsu et al. |
| 6,484,055 B1 | 11/2002 | Marcovecchio |
| 6,493,579 B1 | 12/2002 | Gilkerson et al. |
| 6,512,940 B1 | 1/2003 | Brabec et al. |
| 6,522,917 B1 | 2/2003 | Hsu et al. |
| 6,526,313 B2 | 2/2003 | Sweeney et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,081 B2 | 5/2005 | Hsu |
| 6,959,212 B2 | 10/2005 | Hsu et al. |
| 6,978,177 B1 | 12/2005 | Chen et al. |
| 6,996,434 B2 | 2/2006 | Marcovecchio et al. |
| 7,031,764 B2 | 4/2006 | Schwartz et al. |
| 7,039,463 B2 | 5/2006 | Marcovecchio |
| 7,177,685 B2 | 2/2007 | Lincoln et al. |
| 7,184,818 B2 | 2/2007 | Kim et al. |
| 7,203,535 B1 | 4/2007 | Hsu et al. |
| 7,430,446 B2 | 9/2008 | Li |
| 7,653,430 B2 | 1/2010 | Marcovecchio et al. |
| 7,912,545 B2 | 3/2011 | Li et al. |
| 7,953,476 B2 | 5/2011 | Marcovecchio |
| 2002/0032469 A1 | 3/2002 | Marcovecchio |
| 2002/0049474 A1 | 4/2002 | Marcovecchio et al. |
| 2002/0087091 A1 | 7/2002 | Koyrakh et al. |
| 2002/0091333 A1 | 7/2002 | Hsu et al. |
| 2002/0183637 A1 | 12/2002 | Kim et al. |
| 2002/0183639 A1 | 12/2002 | Sweeney et al. |
| 2002/0198461 A1 | 12/2002 | Hsu et al. |
| 2003/0060849 A1 | 3/2003 | Hsu |
| 2003/0074026 A1 | 4/2003 | Thompson et al. |
| 2003/0083586 A1 | 5/2003 | Ferek-Petric |
| 2003/0083587 A1 | 5/2003 | Ferek-Petric |
| 2003/0100923 A1 | 5/2003 | Bjorling et al. |
| 2003/0109792 A1 | 6/2003 | Hsu et al. |
| 2003/0120316 A1 | 6/2003 | Spinelli et al. |
| 2003/0181818 A1 | 9/2003 | Kim et al. |
| 2004/0015090 A1 | 1/2004 | Sweeney et al. |
| 2004/0093035 A1 | 5/2004 | Schwartz et al. |
| 2004/0116972 A1 | 6/2004 | Marcovecchio |
| 2004/0127806 A1 | 7/2004 | Sweeney |
| 2004/0176694 A1 | 9/2004 | Kim et al. |
| 2005/0010257 A1 | 1/2005 | Lincoln et al. |
| 2005/0015978 A1 | 1/2005 | Andersen et al. |
| 2005/0256544 A1 | 11/2005 | Thompson |
| 2006/0079796 A1 | 4/2006 | Marcovecchio et al. |
| 2006/0095083 A1 | 5/2006 | Zhang et al. |
| 2006/0122527 A1 | 6/2006 | Marcovecchio |
| 2006/0155201 A1 | 7/2006 | Schwartz et al. |
| 2006/0161069 A1 | 7/2006 | Li |
| 2006/0281998 A1 | 12/2006 | Li |
| 2009/0292332 A1 | 11/2009 | Li et al. |
| 2010/0113953 A1 | 5/2010 | Marcovecchio et al. |
| 2011/0034817 A1 | 2/2011 | Marcovecchio |

FOREIGN PATENT DOCUMENTS

| | | |
|---|---|---|
| EP | 0469817 A2 | 2/1992 |
| EP | 0506230 A1 | 9/1992 |
| EP | 554208 A2 | 8/1993 |
| EP | 0711531 A1 | 5/1996 |
| EP | 0776631 A1 | 11/1996 |
| EP | 0848965 A2 | 6/1998 |
| WO | WO-97/39681 A1 | 10/1997 |
| WO | WO-98/40010 | 9/1998 |
| WO | WO-98/53879 | 12/1998 |
| WO | WO-01/26733 A1 | 4/2001 |

OTHER PUBLICATIONS

Duru, F., et al., "The Potential for Inappropriate Ventricular Tachycardia Confirmation Using the Intracardiac Electrogram (EGM) Width Criterion", *Pacing and Clinical Electrophysiology*, 22(7), (Jul. 1999), 1039-1046.

Morris, M. M., "Detection of Atrial Arrhythmia for Cardiac Rhythm Management by Implantable Devices", *Journal of Electrocardiology*, 33, (2000), 133-139.

Schwartz, M., et al., "Cardiac Rhythm Management Systems and Methods Using Multiple Morphology Templates for Discriminating Between Rhythms", U.S. Appl. No. 11/277,095, filed Mar. 21, 2006, 35 pgs.

U.S. Appl. No. 13/195,559, filed Aug. 1, 2011, Discrimination of Supra Ventricular Tachycardia and Ventricular Tachycardia Events.

U.S. Appl. No. 13/208,252, filed Aug. 11, 2011, System for Verifying the Integrity of Cardiac Complex Templates.

METHOD AND APPARATUS FOR CARDIAC ARRHYTHMIA CLASSIFICATION USING TEMPLATE BAND-BASED MORPHOLOGY ANALYSIS

CROSS-REFERENCE TO RELATED APPLICATIONS

This application is a continuation of U.S. patent application Ser. No. 11/038,996, filed Jan. 20, 2005, now issued as U.S. Pat. No. 7,430,446 which is hereby incorporated by reference in its entirety.

This application is related to commonly assigned U.S. Pat. No. 7,039,463, entitled "DISCRIMINATION OF SUPRAVENTRICULAR TACHYCARDIA AND VENTRICULAR TACHYCARDIA EVENTS," filed on Dec. 9, 2003, U.S. Pat. No. 7,031,764, entitled "CARDIAC RHYTHM MANAGEMENT SYSTEMS AND METHODS USING MULTIPLE MORPHOLOGY TEMPLATES FOR DISCRIMINATING BETWEEN RHYTHMS," filed on Nov. 8, 2002, U.S. Pat. No. 6,959,212, entitled "SYSTEM AND METHOD FOR ARRHYTHMIA DISCRIMINATION," filed on Oct. 22, 2001, and U.S. Pat. No. 6,996,434, entitled "METHOD AND SYSTEM FOR VERIFYING THE INTEGRITY OF NORMAL SINUS RHYTHM TEMPLATES," filed Aug. 2, 2001, which are hereby incorporated by reference in their entirety.

TECHNICAL FIELD

This document relates generally to cardiac rhythm management (CRM) systems and particularly, but not by way of limitation, to such a system providing for morphology-based classification of tachyarrhythmias.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachyarrhythmia (also referred to as tachyarrhythmia) occurs when the heart contracts at a rate higher than a normal heart rate. Tachyarrhythmia generally includes ventricular tachyarrhythmia (VT) and supraventricular tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT includes physiologic sinus tachyarrhythmia and pathologic SVTs. The physiologic sinus tachyarrhythmia occurs when the SA node generates the electrical impulses at a particularly high rate. A pathologic SVT occurs, for example, when a pathologic conduction loop forms in an atrium. Fibrillation occurs when the heart contracts at a tachyarrhythmia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as a SVT with an irregular rhythm, though not directly life threatening, also needs medical treatment such as atrial defibrillation to restore a normal cardiac function and to prevent the deterioration of the heart.

Implantable cardioverter/defibrillators (ICDs) are used to treat tachyarrhythmias, including fibrillation. To deliver an effective cardioversion/defibrillation therapy, the cardioversion/defibrillation energy is to be delivered to the chambers of the heart where the tachyarrhythmia or fibrillation originates. When the atrial rate of depolarizations (or contractions) is substantially different from the ventricular rate of depolarizations (or contractions), the atrial and ventricular rates of depolarizations (or contractions) provide for a basis for locating where the tachyarrhythmia originates. However, there is a need to locate where the tachyarrhythmia originates when the atrial depolarizations and the ventricular depolarizations present a one-to-one (1:1) relationship.

SUMMARY

An implantable cardioverter/defibrillator (ICD) includes a tachyarrhythmia detection and classification system that classifies tachyarrhythmias based on a morphological analysis of arrhythmic waveforms and a template waveform. Correlation coefficients each computed between morphological features of an arrhythmic waveform and morphological features of the template waveform provide for the basis for classifying the tachyarrhythmia.

In one embodiment, a system for classifying tachyarrhythmias includes a feature vector generation circuit, a correlation computing circuit, and a beat classification circuit. The feature vector generation circuit produces a template feature vector (a), an arrhythmic feature vector (b), a maximum feature vector ($a_{max}$), and a minimum feature vector ($a_{min}$). The template feature vector (a) is produced based on a plurality of template morphological features on a plurality of template waveforms each associated a template heart beat of a known type cardiac rhythm. The arrhythmic feature vector (b) is produced based on a plurality of arrhythmic morphological features of an arrhythmic waveform associated with an arrhythmic heart beat sensed during a tachyarrhythmia. The maximum feature vector ($a_{max}$) and the minimum feature vector ($a_{min}$) are produced based on the plurality of template morphological features, the plurality of arrhythmic morphological features, and a feature variation vector ($\delta$) related to predetermined confidence levels of the template morphological features. The template feature vector (a) and the feature variation vector ($\delta$) form a template band indicative of morphological variations among the plurality of template morphological features. The maximum feature vector ($a_{max}$) and the minimum feature vector ($a_{min}$) are within this template band. The correlation computing circuit calculates a mean feature correlation coefficient ($Fcc_{mean}$), a maximum feature correlation coefficient ($Fcc_{max}$), and a minimum feature correlation coefficient ($Fcc_{min}$). The mean feature correlation coefficient (Fcc$_{mean}$) is calculated based on the template feature vector (a) and the arrhythmic feature vector (b). The maximum feature correlation coefficient (Fcc$_{max}$) is calculated based on the maximum feature vector (a$_{max}$) and the arrhythmic feature vector (b). The minimum feature correlation coefficient (Fcc$_{min}$) is calculated based on the minimum feature vector (a$_{min}$) and the arrhythmic feature vector (b). The beat classification circuit classifies the arrhythmic heart beat based on the mean feature correlation coefficient (Fcc$_{mean}$), the maximum feature correlation coefficient (Fcc$_{max}$), the minimum feature correlation coefficient (Fcc$_{min}$), and at least one predetermined correlation threshold.

In one embodiment, a morphology-based method for classifying tachyarrhythmias using a template band is provided. A template feature vector (a) and a template standard deviation vector (σ) are produced based on template morphological features on a plurality of template waveforms each associated with a heart beat of a known type cardiac rhythm. An arrhythmic feature vector (b) is produced based on arrhythmia morphological features on an arrhythmic waveform associated with an arrhythmic heart beat sensed during a tachyarrhythmia. A maximum deviation vector (x$_{max}$) and a minimum deviation vector (x$_{min}$) are produced based on at least the template feature vector (a), the arrhythmic feature vector (b), and the template standard deviation vector (σ). The maximum deviation vector (x$_{max}$) and the minimum deviation vector (x$_{min}$) are indicative of morphological variations among the plurality of template morphological features. Then, a maximum feature vector (a$_{max}$) is produced by adding the maximum deviation vector (x$_{max}$) to the template feature vector (a), and a minimum feature vector (a$_{min}$) is produced by adding the minimum deviation vector (x$_{min}$) to the template feature vector (a). A mean feature correlation coefficient (Fcc$_{mean}$) is computed based on the template feature vector (a) and the arrhythmic feature vector (b). A maximum feature correlation coefficient (Fcc$_{max}$) is computed based on the maximum feature vector (a$_{max}$) and the arrhythmic feature vector (b). A minimum feature correlation coefficient (Fcc$_{min}$) is computed based on the minimum feature vector (a$_{min}$) and the arrhythmic feature vector (b).

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
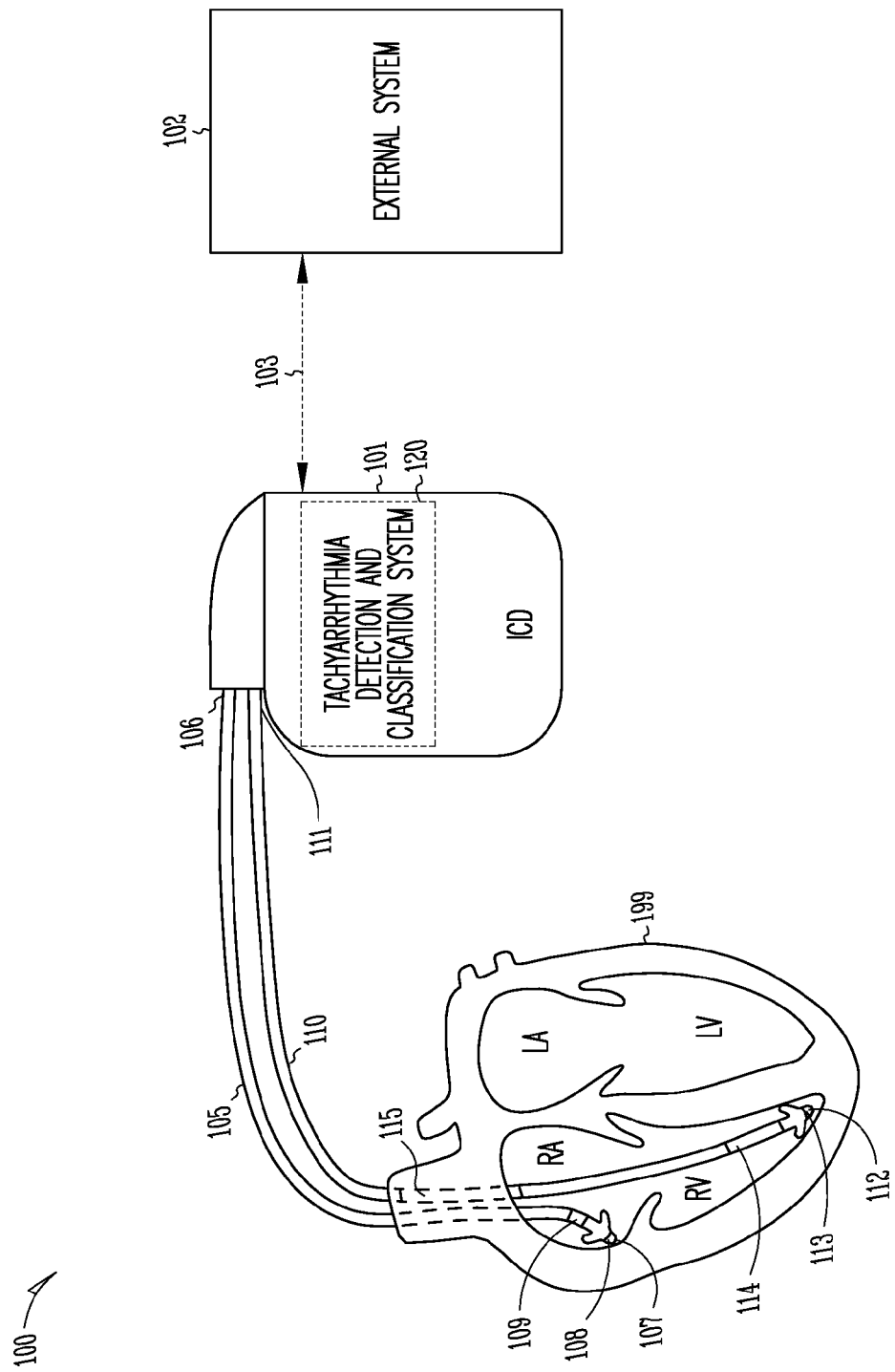
FIG. 1 is an illustration of one embodiment of a CRM system and portions of the environment in which CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

A "circuit" in this document includes, but is not limited to, an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator circuit" includes, among other things, an electronic circuit comparator constructed to perform the only function of a comparison between two signals or a portion of a general-purpose circuit driven by a code instructing that portion of the general-purpose circuit to perform the comparison between the two signals.

In this document, an "arrhythmic heart beat" includes a heart beat sensed during a detected tachyarrhythmic episode. An "arrhythmic waveform" includes a waveform (such as a segment of an electrogram) associated with an arrhythmic heart beat. "Arrhythmic morphological features" include morphological features of an arrhythmic waveform. An "arrhythmic feature vector" includes a vector associated with a plurality of arrhythmic morphological features of an arrhythmic waveform. For example, an arrhythmic feature vector $x=[x_1, x_2, \ldots x_N]$, where $x_1, x_2, \ldots x_N$ are each associated with one arrhythmic morphology feature of the arrhythmic waveform. In a specific example, $x_1, x_2, \ldots x_N$ are each an amplitude of the arrhythmic waveform measured at the locations of the arrhythmic morphological features. A "template heart beat" represents a heart beat associated with a known rhythm and used as a "template" for a morphological analysis using morphological features associated with the known rhythm. The template heart beat may be produced from a plurality of hearts beats sensed during the known rhythm, such as by averaging. A "template waveform" includes a waveform associated with the template heart beat. "Template morphological features" include morphological features of the template waveform. A "template feature vector" includes a vector associated with a plurality of template morphological features of the template waveform. For example, a template feature vector $y=[y_1, y_2, \ldots y_N]$, where $y_1, y_2, \ldots y_N$ are each associated with one template morphology feature of the template waveform. In a specific example, $y_1, y_2, \ldots y_N$ are each an amplitude of the template waveform measured at the locations of the template morphological features.

In this document, "mean" (such as in a "mean feature correlation coefficient") includes mean and other notations of central tendency, such as average and median.

This document discusses, among other things, a CRM system including a circuit for further classifying a detected cardiac arrhythmia including, but not being limited to, a 1:1 tachyarrhythmia. The 1:1 tachyarrhythmia, characterized by an approximately one-to-one association between atrial and ventricular depolarizations, is indicated by substantially equal atrial and ventricular rates. The 1:1 tachyarrhythmia is further classified based on a morphological analysis of arrhythmic waveforms and a template waveform each being a segment of a cardiac signal such as an electrogram. It is to be understood that while the classification of the 1:1 tachyarrhythmia is specifically discussed throughout this document as examples, the methods and apparatuses according to the present subject matter are also applicable in morphology-based classification of cardiac arrhythmias other than the 1:1 tachyarrhythmia.

FIG. 1 is an illustration of one embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to ICD 101 and a distal end 107 disposed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow sensing of the atrial electrogram and/or delivery of atrial pacing pulses. Lead 110 is a defibrillation lead that includes a proximal end 111 connected to ICD 101 and a distal end 112 disposed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses.

ICD 101 includes a tachyarrhythmia detection and classification system 120 that includes a morphology-based 1:1 tachyarrhythmia discrimination circuit. An exemplary embodiment of a circuit of system 120 is discussed below with reference to FIG. 2. System 120 detects and classifies 1:1 tachyarrhythmias by using a morphology-based 1:1 tachyarrhythmia discrimination method introduced below with reference to FIG. 3. Depending on the outcome of the tachyarrhythmia detection and classification, system 120 determines whether to deliver a pacing and/or cardioversion/defibrillation therapy. In one embodiment, system 120 delivers a ventricular defibrillation pulse when a 1:1 tachyarrhythmia is classified as a VT.

External system 102 allows for programming of ICD 101 and receives signals acquired by ICD 101. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system allows access to ICD 101 from a remote location, such as for monitoring patient status and adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing the morphology-based 1:1 tachyarrhythmia discrimination method discussed in this document), and programming ICD 101 to deliver pacing and/or cardioversion/defibrillation therapies.

Figure 2:
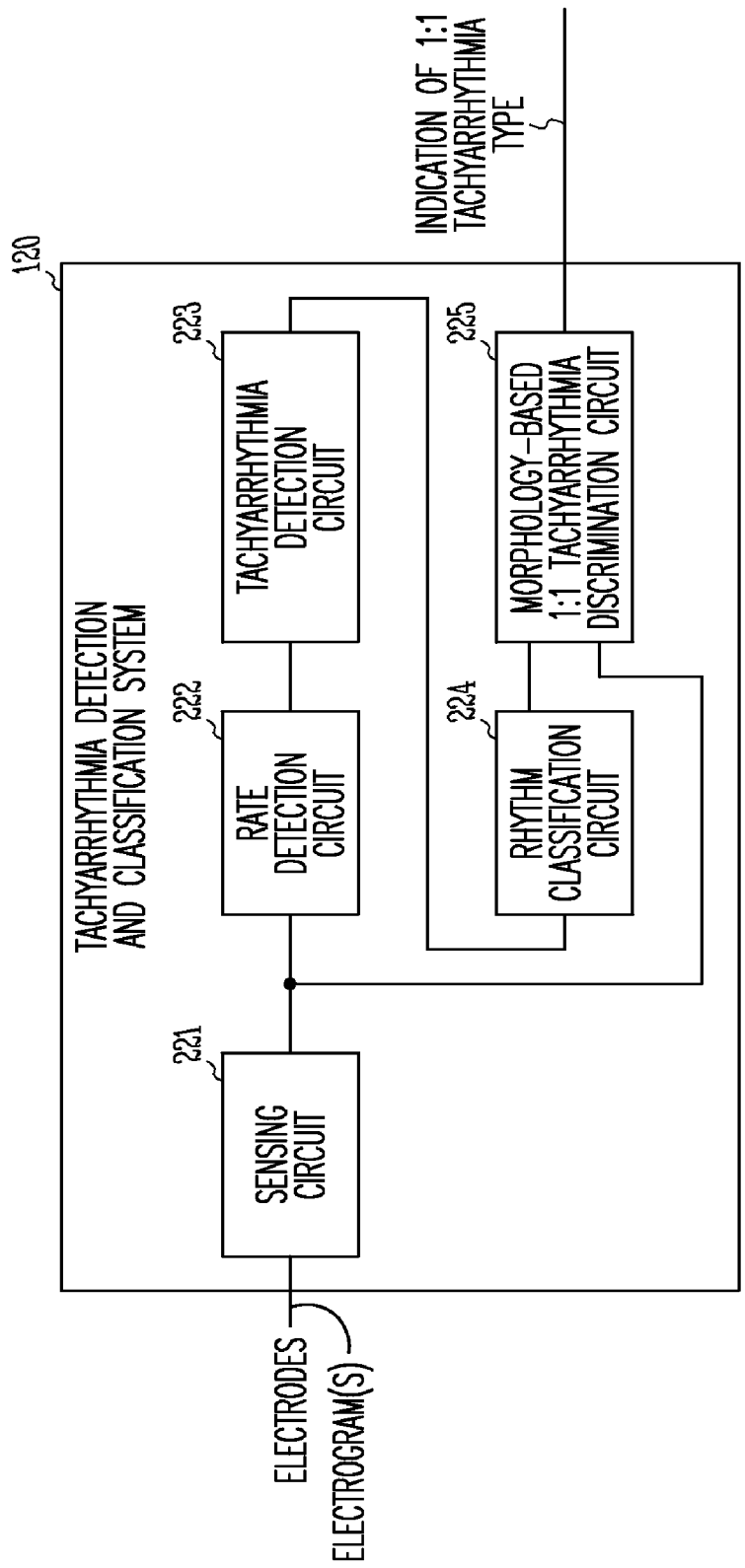
FIG. 2 is a block diagram illustrating an embodiment of a tachyarrhythmia detection and classification system being part of the CRM system.

FIG. 2 is a block diagram illustrating an embodiment of a circuit of system 120. System 120 includes a sensing circuit 221, a rate detection circuit 222, a tachyarrhythmia detection circuit 223, a rhythm classification circuit 224, and a morphology-based 1:1 tachyarrhythmia discrimination circuit 225. Sensing circuit 221 is electrically coupled to a heart to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization. Rate detection circuit 222 detects an atrial rate based on the atrial electrogram and a ventricular rate based on the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute. Tachyarrhythmia detection circuit 223 detects a tachyarrhythmia based on at least one of the atrial rate and the ventricular rate. In one embodiment, the tachyarrhythmia is detected when the atrial rate exceeds a predetermined tachyarrhythmia threshold rate. In another embodiment, the tachyarrhythmia is detected when the ventricular rate exceeds a predetermined tachyarrhythmia threshold rate. Rhythm classification circuit 224 classifies the detected tachyarrhythmia as a 1:1 tachyarrhythmia when the atrial rate and the ventricular rate are substantially equal. In one embodiment, rhythm classification circuit 224 classifies the detected tachyarrhythmia as the 1:1 tachyarrhythmia when the difference between the atrial rate and the ventricular rate is between a predetermined limit, such as 10 bpm. Morphology-based 1:1 tachyarrhythmia discrimination circuit 225 further classifies the 1:1 tachyarrhythmia, such as by its origin, by performing one or more methods for morphology-based tachyarrhythmia discrimination discussed in this document.

Figure 3:
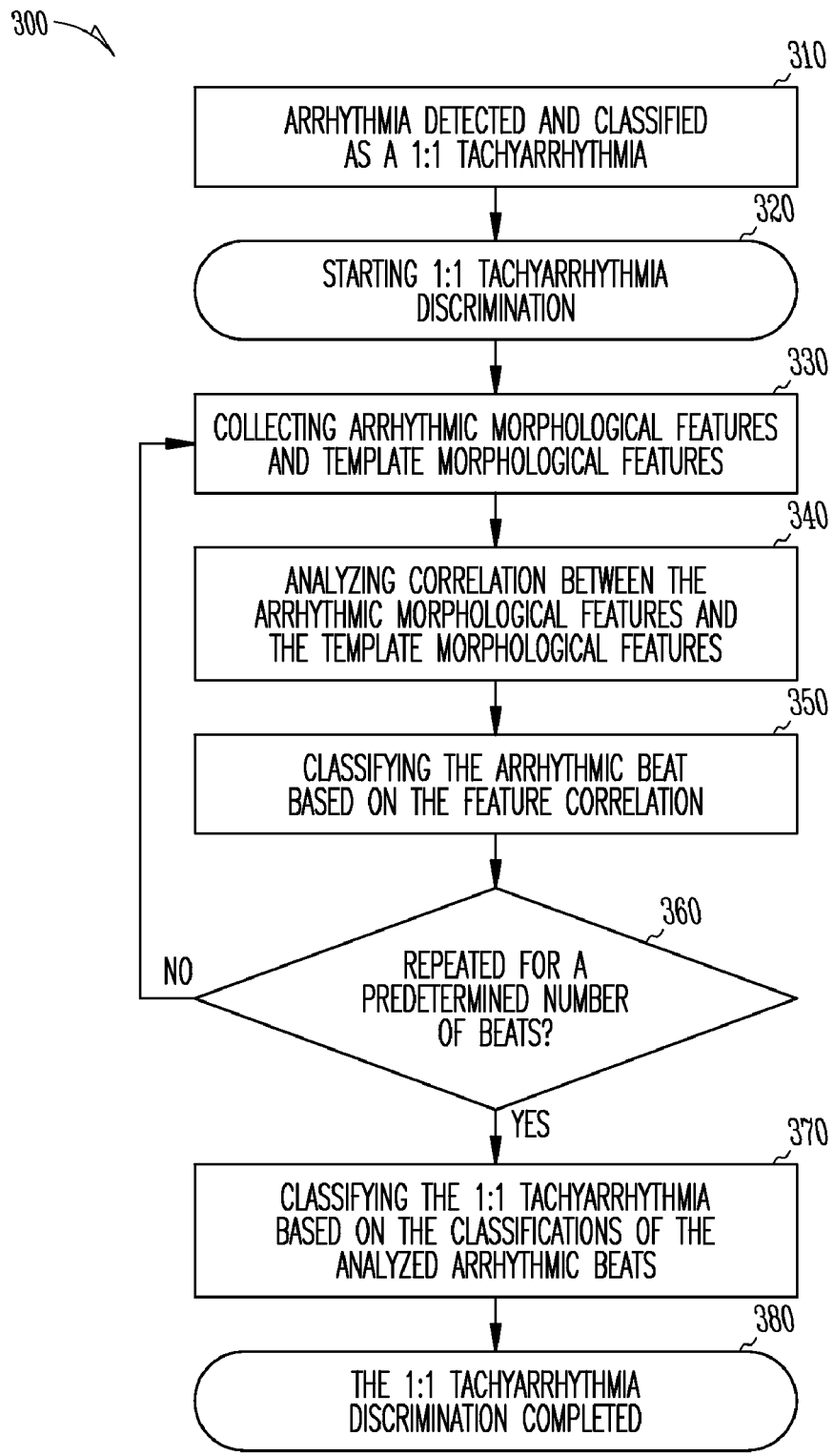
FIG. 3 is a flow chart illustrating an embodiment of a method for morphology-based 1:1 tachyarrhythmia discrimination.

FIG. 3 is a flow chart illustrating an embodiment of a method 300 for morphology-based tachyarrhythmia discrimination. In one embodiment, method 300 is performed by morphology-based 1:1 tachyarrhythmia discrimination circuit 225. After a detected arrhythmia is classified as a 1:1 tachyarrhythmia at 310, a process of discriminating the 1:1 tachyarrhythmia is started at 320.

Arrhythmia morphological features and template morphological features are collected at 330. The morphological features are points in a cardiac signal that have morphological characteristics allowing discrimination between two or more types of 1:1 tachyarrhythmias. In one embodiment, the template heart beat represents a heart beat of a normal sinus rhythm (NSR). In one embodiment, template morphological features are collected from the template heart beat and stored. This includes recording timing and other quantitative information, such as amplitudes, associated with the features. In one specific embodiment, the feature collection is repeated for a plurality of template heart beats, and the timing and other quantitative information associated with the features are averages calculated over the plurality of template heart beats. For discriminating the detected 1:1 tachyarrhythmia, arrhythmic morphological features are extracted from the arrhythmic heart beat by temporal correspondence with the template morphological features of the template heart beat. A set of template morphological features and a set of corresponding arrhythmic morphological features are thus collected for the correlation analysis that follows. In another embodiment, a template waveform is stored. For discriminating the detected 1:1 tachyarrhythmia, arrhythmic morphological features are collected from the arrhythmic heart beat. Then, template morphological features are extracted from the stored template waveform at the locations temporally corresponding to the locations of the arrhythmic morphological features on the arrhythmic waveform. A set of template morphological features and a set of arrhythmic morphological features are thus collected for the correlation analysis that follows. In one specific embodiment, the template waveform is averaged over a plurality of template heart beats.

Correlation between the arrhythmic morphological features and the template morphological features is analyzed at 340. The correlation analysis results in one or more correlation coefficients associated with each arrhythmic heart beat. One example for calculating such a correlation coefficient, referred to as a feature correlation coefficient (Fcc), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety.

The arrhythmic heart beat is classified based on the one or more correlation coefficients at 350. In one embodiment, each correlation coefficient is compared to one or more thresholds defining detection windows each corresponding to one type of 1:1 tachyarrhythmia. In another embodiment, a score is produced based on the one or more correlation coefficients to provide a measure of the probability that the 1:1 tachyarrhythmia is of a known particular type. Examples of the known particular types of 1:1 tachyarrhythmia include, but are not limited to, supraventricular tachyarrhythmia (SVT), ventricular tachyarrhythmia (VT), monomorphic VT (MVT), and polymorphic VT (PVT).

The feature collection and correlation are repeated for a predetermined number of arrhythmic heart beats. If the predetermined number has not been reached at 350, steps 330 through 340 are repeated for the next arrhythmic heart beat.

After the predetermined number has been reached at 360, the 1:1 tachyarrhythmia is classified based on the classification given to the analyzed arrhythmic heart beats at 370. In one embodiment, the 1:1 tachyarrythmia is classified by a majority voting. That is, the 1:1 tachyarrhythmia is classified as a tachyarrhythmia of a particular type if a majority of the analyzed arrhythmic heart beats are classified as the tachyarrhythmia of that particular type. In one specific embodiment, 80% (such as 8 out of 10 analyzed arrhythmic heart beats) is considered as the majority. For example, to discriminate between VT and SVT using an NSR beat as the template heart beat, if 8 out of 10 arrhythmic heart beats are classified as VT beats, the tachyarrhythmia is classified as a VT rhythm. Otherwise, it is classified as a SVT rhythm. In another specific embodiment, 60% is considered as the majority. In another embodiment, in which a score is produced to provide a measure of the likeliness that the 1:1 tachyarrhythmia is of a known particular type, the scores produced for all the analyzed arrhythmic heart beats are averaged or otherwise processed to provide an indication for the type of the 1:1 tachyarrhythmia.

The discrimination of the 1:1 tachyarrhythmia is completed at 380, with a classification of the 1:1 tachyarrhythmia being indicated. In one embodiment, the classification provides for a basis for making a therapeutic decision. For example, if a 1:1 tachyarrhythmia is classified as a VT, a ventricular defibrillation pulse is delivered.

In one embodiment of step 330, a dynamic beat-driven morphological feature extraction method is provided. Arrhythmic morphological features are collected from an arrhythmic waveform sensed while a 1:1 tachyarrhythmia is indicated. The arrhythmic morphological features include points on the arrhythmic waveform that have detectable morphological characteristics, such as points being or related to peak points and/or turning points. The temporal relationship between each feature and a fiducial point such as a peak of a depolarization is then determined for the arrhythmic heart beat. This temporal relationship is then used to sample a pre-stored template waveform. This results in a set of arrhythmic morphological features and a corresponding set of template morphological features. The dynamic beat-driven morphological feature extraction is discussed in detail below, with reference to FIGS. 5-9.

In one embodiment of steps 330 through 370, a template band-based correlation analysis and a fuzzy discrimination process are provided. The template band is created for the correlation analysis based on the morphological variations in a plurality of template heart beats. The template band includes template morphological features with confidence intervals. The correlation analysis is performed using the template band and the arrhythmic morphological features extracted from an arrhythmic heart beat. This correlation analysis results in a plurality of correlation coefficients representing a range of correlation coefficients associated with that arrhythmic heart beat. A fuzzy score is then calculated based on the correlation coefficients for the arrhythmic heart beat. The 1:1 tachyarrhythmia is classified based on the fuzzy scores calculated for all the analyzed arrhythmic heart beats.

The template band-based correlation analysis and the fuzzy discrimination are further discussed below, with reference to FIGS. 10-15.

In another embodiment of step 340, a Mahalanobis distance-based correlation analysis method is provided. The correlation analysis produces Mahalanobis distance-based correlation coefficients for use in the classification of the 1:1 tachyarrhythmia. The Mahalanobis distance-based correlation analysis takes account the variability of and co-variability between template morphological features. It allows for a more robust classification of the 1:1 tachyarrhythmia than a Euclidean distance-based correlation analysis. The Mahalanobis distance-based correlation analysis is further discussed below, with reference to FIGS. 16-20.

In one embodiment of step 370, a method for discriminating the 1:1 tachyarrhythmia based on stability of morphology is provided. In addition to the correlation analysis, the stability of the morphology is analyzed to discriminate the 1:1 tachyarrhythmia. The variance of the correlation coefficients produced by the correlation analysis for the analyzed arrhythmic heart beats is analyzed to discriminate the 1:1 tachyarrhythmia. The morphological stability analysis is further discussed below, with reference to FIGS. 21-25.

It is to be understood that the embodiments discussed above are not necessarily combined for use in a single CRM system. As those skilled in the art will understand upon reading and comprehending this document, a CRM system for classifying 1:1 tachyarrhythmias may perform any one or more of the dynamic beat-driven morphological feature extraction, the template band-based correlation analysis and the fuzzy discrimination, the Mahalanobis distance-based correlation analysis, and the morphological stability analysis in the tachyarrhythmia detection and classification.

Figure 4:
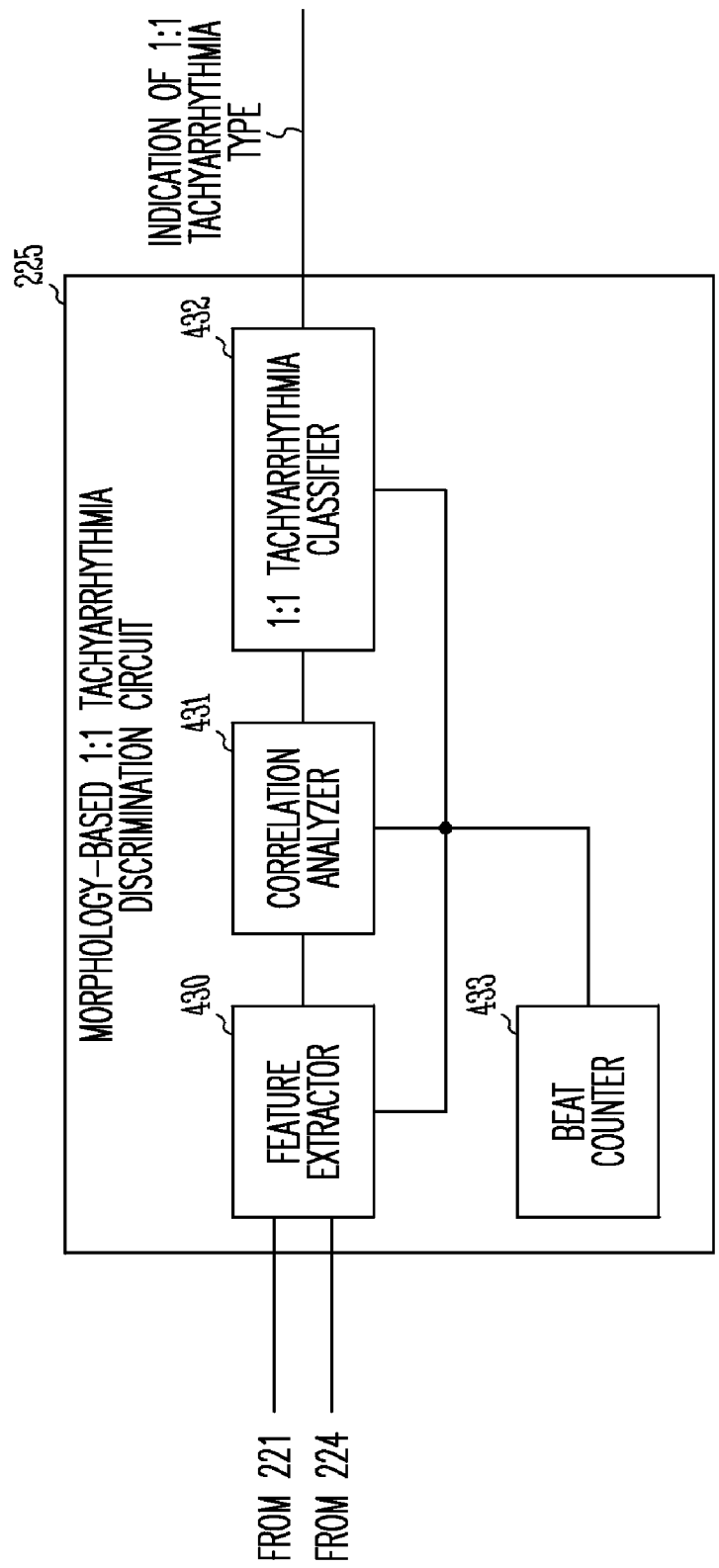
FIG. 4 is a block diagram illustrating an embodiment of a morphology-based 1:1 tachyarrhythmia discrimination circuit being part of the tachyarrhythmia detection and classification system.

FIG. 4 is a block diagram illustrating an embodiment of morphology-based 1:1 tachyarrhythmia discrimination circuit 225. Morphology-based 1:1 tachyarrhythmia discrimination circuit 225 includes a feature extractor 430, a correlation analyzer 431, a 1:1 tachyarrhythmia classifier 432, and a beat counter 433. Feature extractor 430 extracts features a waveform associated with a heart beat. Correlation analyzer 431 computes a correlation coefficient between arrhythmic morphological features of an arrhythmic beat of a 1:1 tachyarrhythmia and template morphological features of a beat of a known type cardiac rhythm. In one embodiment, correlation analyzer 431 computes the feature correlation coefficient (Fcc) for each arrhythmic beat of a plurality of arrhythmic beats sensed during a detected tachyarrhythmia. Beat counter 433 counts the number of arrhythmic heart beats for which the arrhythmic features are extracted and analyzed. Based on the correlation coefficients calculated for a predetermined number of arrhythmic heart beats, 1:1 tachyarrhythmia classifier 432 classifies the 1:1 tachyarrhythmia.

In one embodiment, morphology-based 1:1 tachyarrhythmia discrimination circuit 225 performs the method illustrated in FIG. 3. Feature extractor 430 performs step 330, correlation analyzer 431 performs step 340, and 1:1 tachyarrythmia classifier 432 performs step 360.

Dynamic Beat-Driven Morphological Feature Extraction

Figure 5:
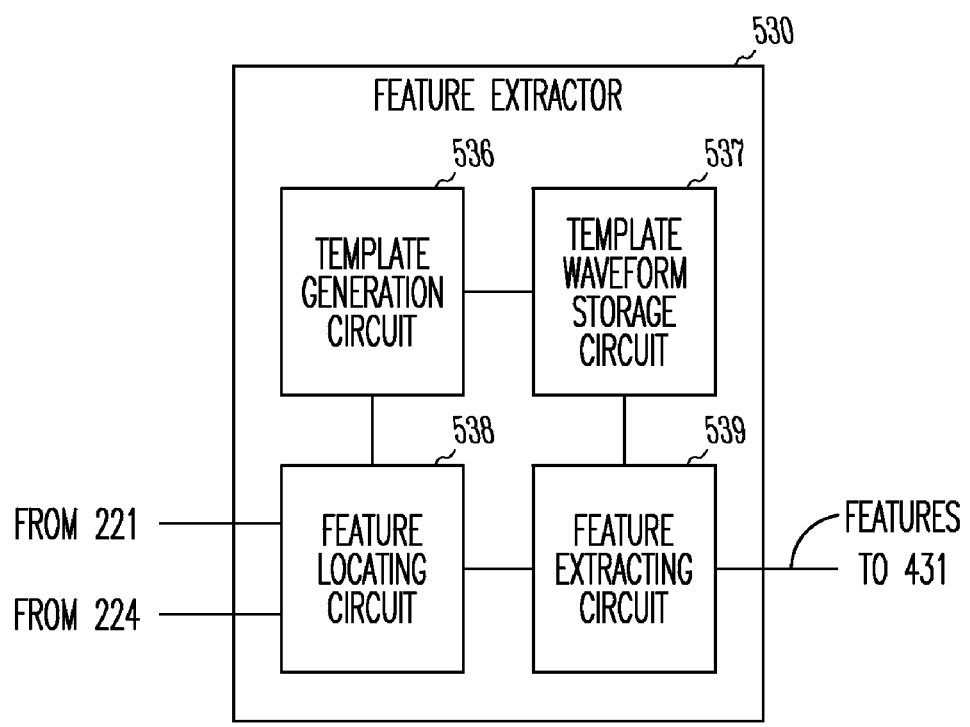
FIG. 5 is a block diagram illustrating an embodiment of a feature extractor being part of the morphology-based 1:1 tachyarrhythmia discrimination circuit.

FIG. 5 is a block diagram illustrating an embodiment of a feature extractor 530. Feature extractor 530 is one embodiment of feature extractor 430 and includes a template generation circuit 536, a template waveform storage circuit 537, a feature locating circuit 538, and a feature extracting circuit 539.

Feature extractor 530 selects arrhythmic morphological features on a waveform of an arrhythmic beat sensed during a detected 1:1 tachyarrhythmia and extracts the temporally corresponding template morphological features from a stored template waveform. Template generation circuit 536 produces a template waveform to represent a template heart beat of a known type cardiac rhythm. Template waveform storage circuit 537 stores that template waveform. After a tachyarrhythmia is detected and classified as a 1:1 tachyarrhythmia, feature locating circuit 538 selects a plurality of arrhythmic morphological features on an arrhythmic waveform of an arrhythmic heart beat sensed during the 1:1 tachyarrhythmia. Feature locating circuit 538 then produces timing information to indicate the locations of these arrhythmic morphological features on the arrhythmic waveform. Feature extracting circuit 539 locates a plurality of template morphological features on the stored template waveform based on the timing information produced by feature locating circuit 538.

Figure 6:
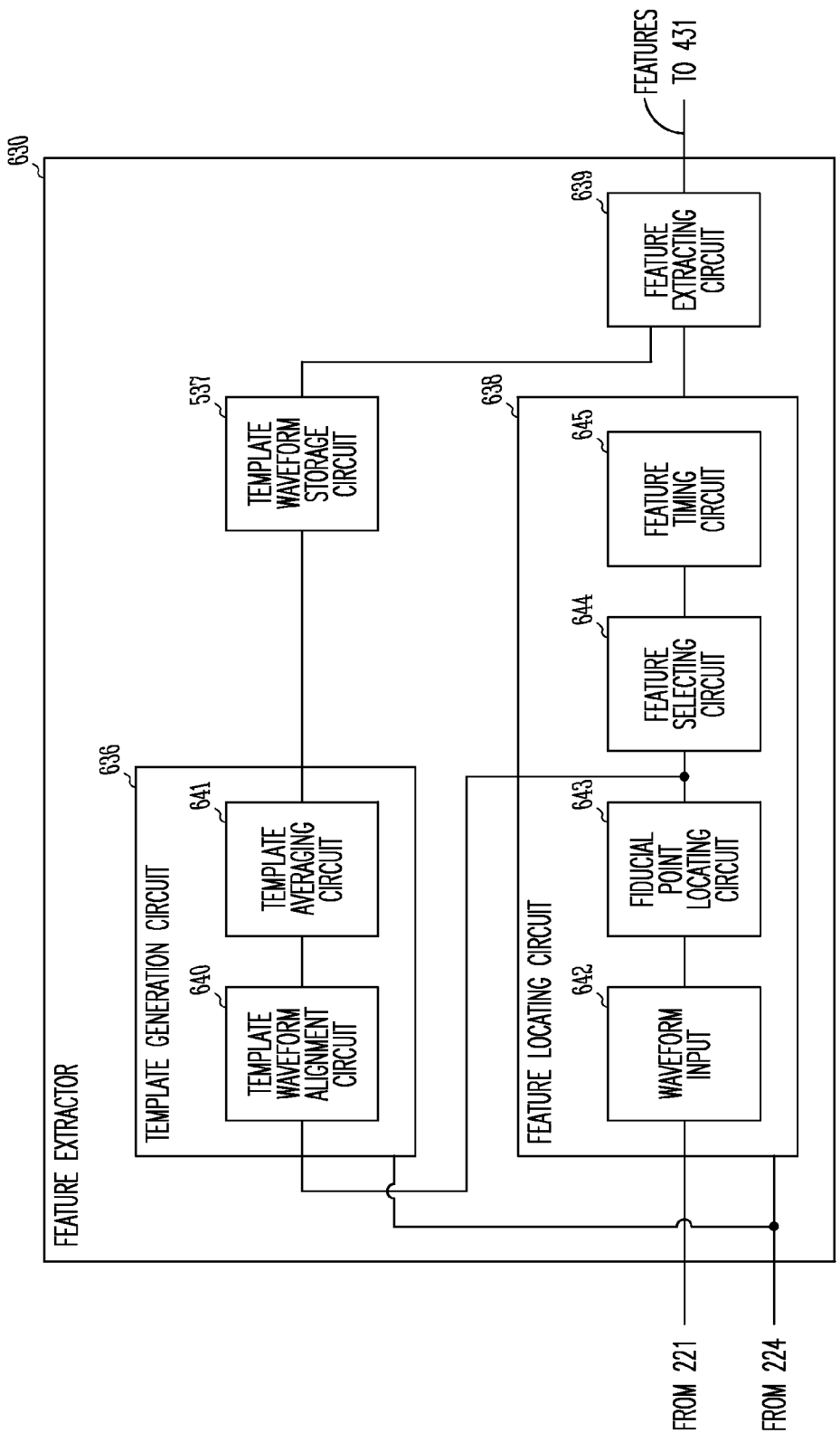
FIG. 6 is a block diagram illustrating a specific embodiment of the feature extractor of FIG. 5.

FIG. 6 is a block diagram illustrating a feature extractor 630, which is a specific embodiment of feature extractor 530. Feature extractor 630 includes a template generation circuit 636, template waveform storage circuit 537, a feature locating circuit 638, and a feature extracting circuit 639.

Template generation circuit 636 is a specific embodiment of template generation circuit 536 and includes a template waveform alignment circuit 640 and a template averaging circuit 641. Template waveform alignment circuit 640 aligns a plurality of template waveforms by a fiducial point. The template waveforms are each associated with a heart beat sensed during a known type cardiac rhythm, such as an NSR. In one embodiment, template waveform alignment circuit 640 includes a peak detector to detect a peak of a depolarization for use as the fiducial point. Template averaging circuit 641 produces the template waveform that will be stored in template waveform storage circuit 537 by averaging the amplitudes of the plurality of template waveforms.

Feature locating circuit 638 is a specific embodiment of feature locating circuit 538 and includes a waveform input 642, a fiducial point locating circuit 643, a feature selecting circuit 644, and a feature timing circuit 645. Waveform input 642 receives the arrhythmic waveform. Fiducial point locating circuit 643 detects a fiducial point on the arrhythmic waveform. In one embodiment, fiducial point locating circuit 643 includes a peak detector to detect a peak of a depolarization from the arrhythmic waveform. In one embodiment, during the generation of the template waveform that will be stored in template waveform storage circuit 537, waveform input 642 also receives the template waveforms, and fiducial point locating circuit 643 also detects the fiducial point on each of the template waveforms for the alignment of the template waveforms. Feature selecting circuit 644 selects a plurality of arrhythmic morphological features on the arrhythmic waveform based on one or more predetermined criteria. Example of the morphological features include, but are not limited to, peaks and other turning points on the arrhythmic waveform, points associated with maximum slopes, and points having a predefined timing relationship with the peaks, other turning points, and/or points associated with maximum slopes. Feature timing circuit 645 measures time intervals each between the fiducial point on the arrhythmic waveform and one of the selected arrhythmic morphological features.

Feature extracting circuit 639 is a specific embodiment of feature extracting circuit 539 and locates the plurality of template morphological features on the template waveform based on the fiducial point on the arrhythmic waveform and the measured time intervals. Feature extracting circuit 639 locates a corresponding fiducial point on the template waveform, aligns the fiducial point on the arrhythmic waveform and the corresponding fiducial point on the template waveform, and locates the template morphological features on the template waveform using the measured time intervals. Each measured time interval is used as a time interval between a template morphological feature and the fiducial point on the template waveform.

Figure 7:
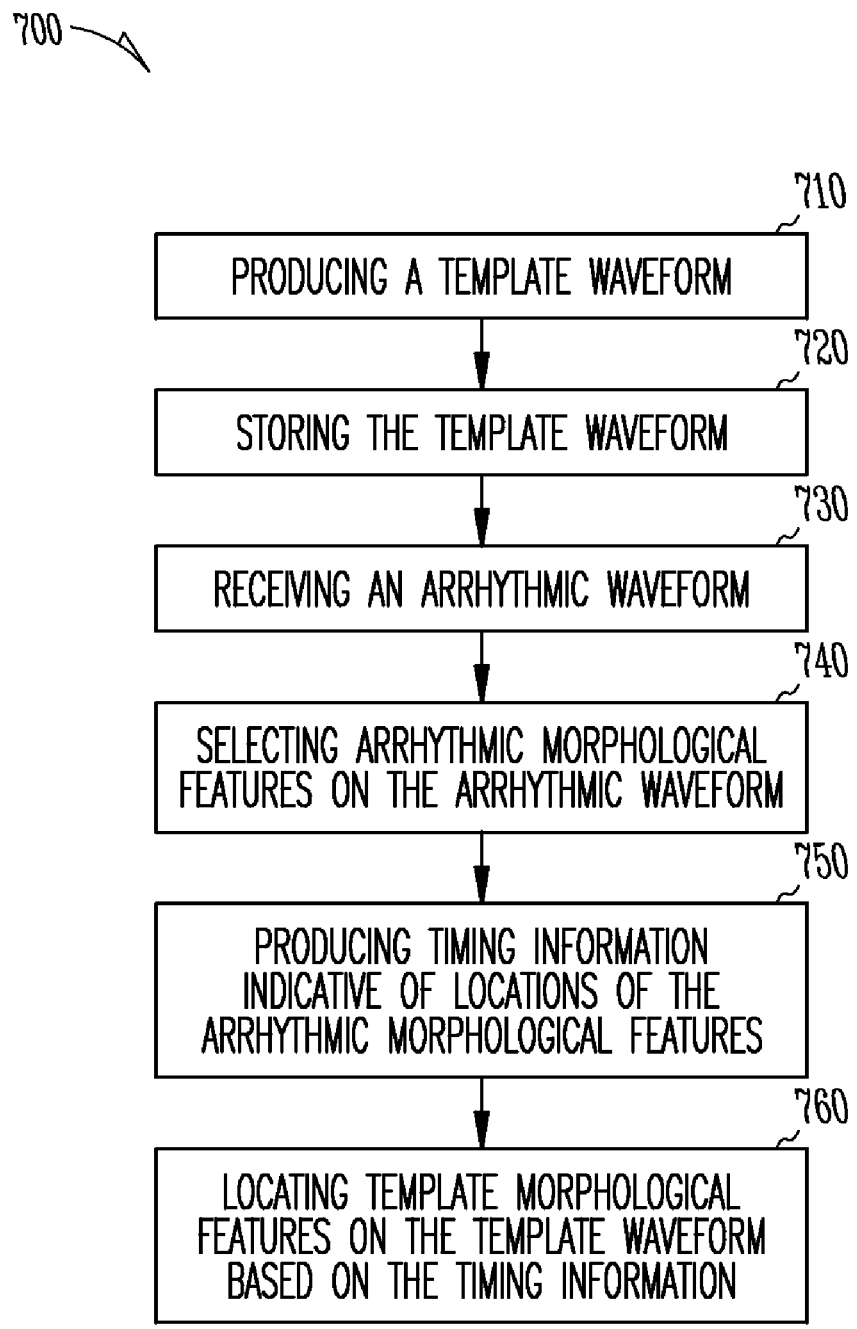
FIG. 7 is a flow chart illustrating an embodiment of a method for extracting morphological features for the morphology-based 1:1 tachyarrhythmia discrimination.

FIG. 7 is a flow chart illustrating an embodiment of a method 700 for extracting morphological features for the morphology-based 1:1 tachyarrhythmia discrimination. In one embodiment, feature extractor 530, including its specific embodiment, feature extractor 630, performs method 700.

A template waveform is produced at 710. The template waveform represents a template heart beat. In one embodiment, multiple waveforms are aligned by a fiducial point and averaged to produce the template waveform. Each waveform is associated with a heart beat that occurs during a known type cardiac rhythm. In one specific embodiment, about 16 waveforms are aligned by a peak of depolarization and averaged to produce the template waveform. Each of the 16 waveforms represents a heart beat that occurs during an NSR. The template waveform is stored at 720 for use in the morphology-based 1:1 tachyarrhythmia discrimination when a tachyarrhythmia is detected and classified as a 1:1 tachyarrhythmia.

An arrhythmic waveform is received at 730. The arrhythmic waveform represents an arrhythmic heart beat that occurs during a 1:1 tachyarrhythmia. A plurality of arrhythmic morphological features are selected from the arrhythmic waveform based on predetermined criteria at 740. The arrhythmic morphological features are characteristic points that are reliably detectable form substantially all the arrhythmic waveforms used in the morphology-based 1:1 tachyarrhythmia discrimination. Timing information indicative of the locations of the arrhythmic morphological features is produced at 750. In one embodiment, a fiducial point, such as a peak of a depolarization, is detected from the arrhythmic waveform. The timing information includes time intervals each measured between the fiducial point and one of the arrhythmic morphological features.

A plurality of template morphological features are located on the template waveform based on the timing information indicative of the locations of the plurality of arrhythmic morphological features at 760. In one embodiment, the template morphological features are located on the template waveform based on the fiducial point and the measured time intervals. A fiducial point corresponding to the fiducial point on the arrhythmic waveform is located on the template waveform. The fiducial points on the arrhythmic and template waveforms are aligned. The template morphological features are located on the template waveform using the measured time intervals. Each measured time interval is used as an interval between one template morphological feature and the fiducial point on the template waveform.

Figure 8:
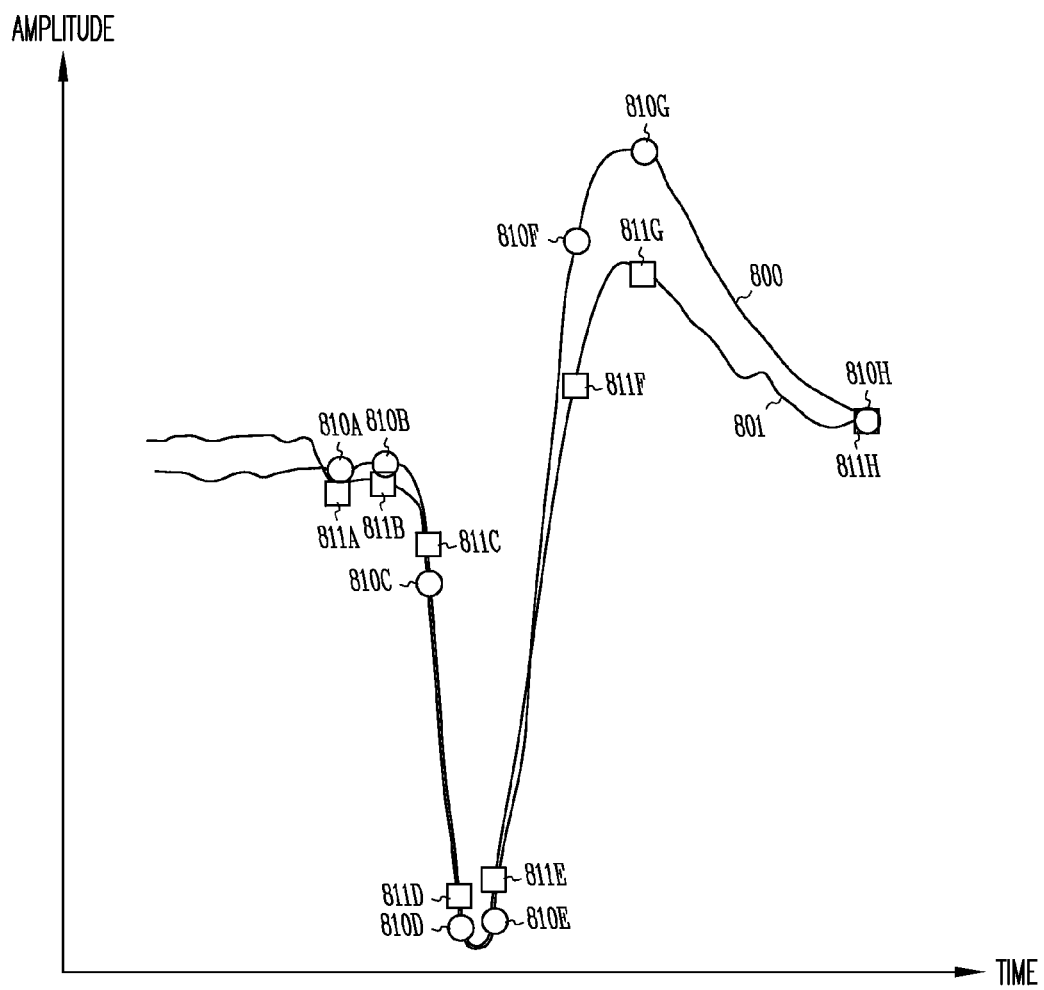
FIG. 8 is a graph illustrating feature extraction using the method of FIG. 7.

FIG. 8 is a graph illustrating feature extraction using method 700. Waveform 800 is an exemplary template waveform. Waveform 801 is an exemplary arrhythmic waveform. Waveforms 800 and 801 are each a segment of a ventricular electrogram showing a ventricular depolarization (R-wave). The two waveforms are temporally aligned by the peak of the R-wave. Arrhythmic morphological features 811A-811H are selected on waveform 801. Corresponding template morphological features 810A-810H are then extracted from waveform 800 as points that are temporally (vertically as shown in FIG. 8) aligned with arrhythmic morphological features 811A-811H.

Figure 9:
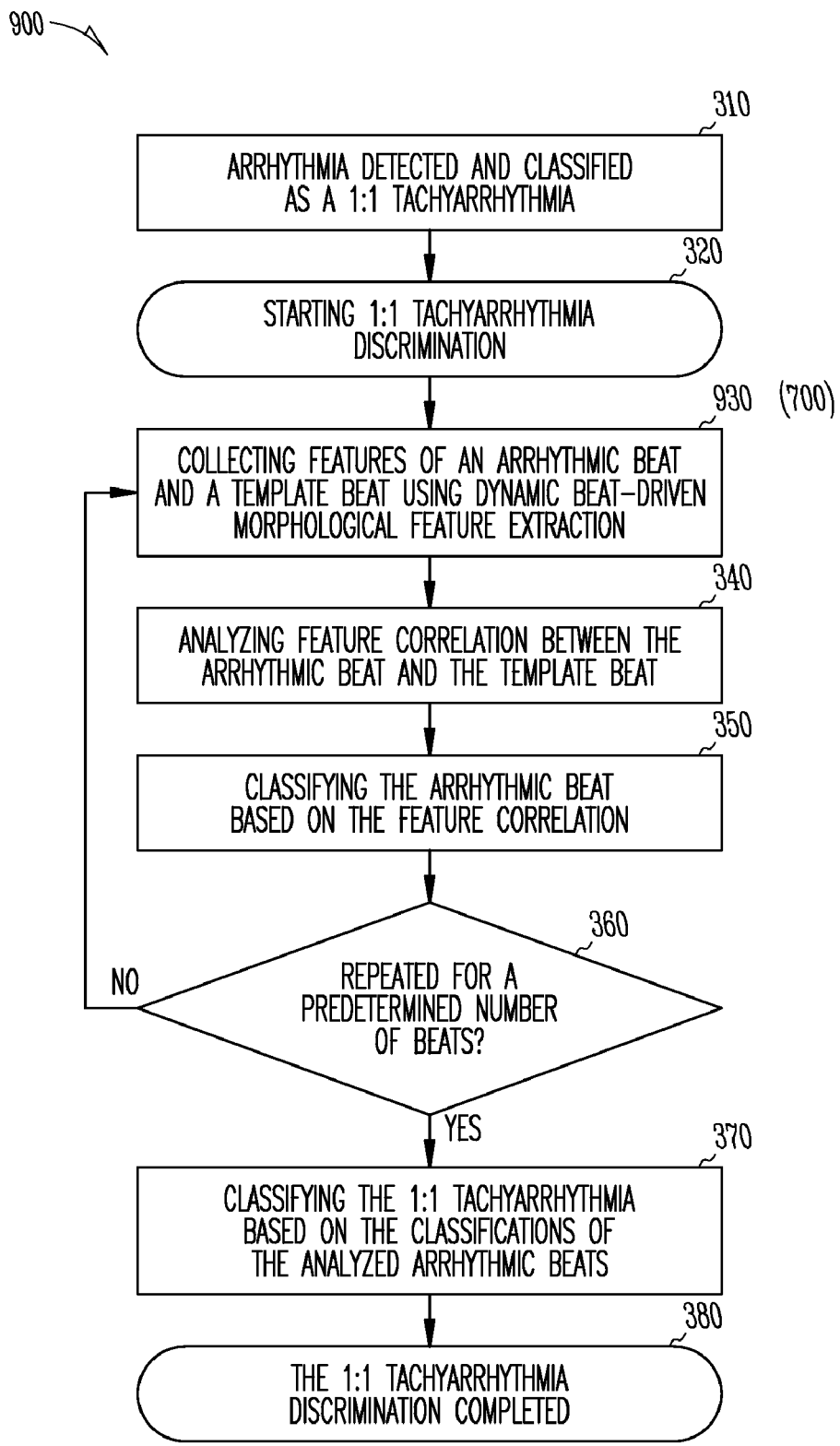
FIG. 9 is a flow chart illustrating a specific embodiment of the method for morphology-based 1:1 tachyarrhythmia discrimination as illustrated in FIG. 3 including an exemplary application of the method of FIG. 7.

FIG. 9 is a flow chart illustrating a method 900 for the morphology-based tachyarrhythmia discrimination. Method 900 is a specific embodiment of method 300 and includes an exemplary application of method 700. Step 930 in method 900 is a specific embodiment of step 330 and includes method 700 as discussed above.

Feature extraction using method 700 in a morphology-based tachyarrhythmia discrimination method such as method 300 has a number of advantages. For example, features extracted from the arrhythmic waveform represent the morphological characteristics of the arrhythmic heart beat with high fidelity. In general, an arrhythmic heart beat is morphologically more complex and less organized than a template heart beat that is a beat of the NSR. Therefore, the locations of the arrhythmic morphological features determined from the arrhythmic waveform represent the morphology of the template heart beat well, possibly with some harmless redundancy in morphological representation. Method 700 also allows variable number of morphological features to be used in the analysis of feature correlation at 340 after the template waveform is generated and stored.

Template Band-Based Correlation Analysis and Fuzzy Discrimination

Figure 10:
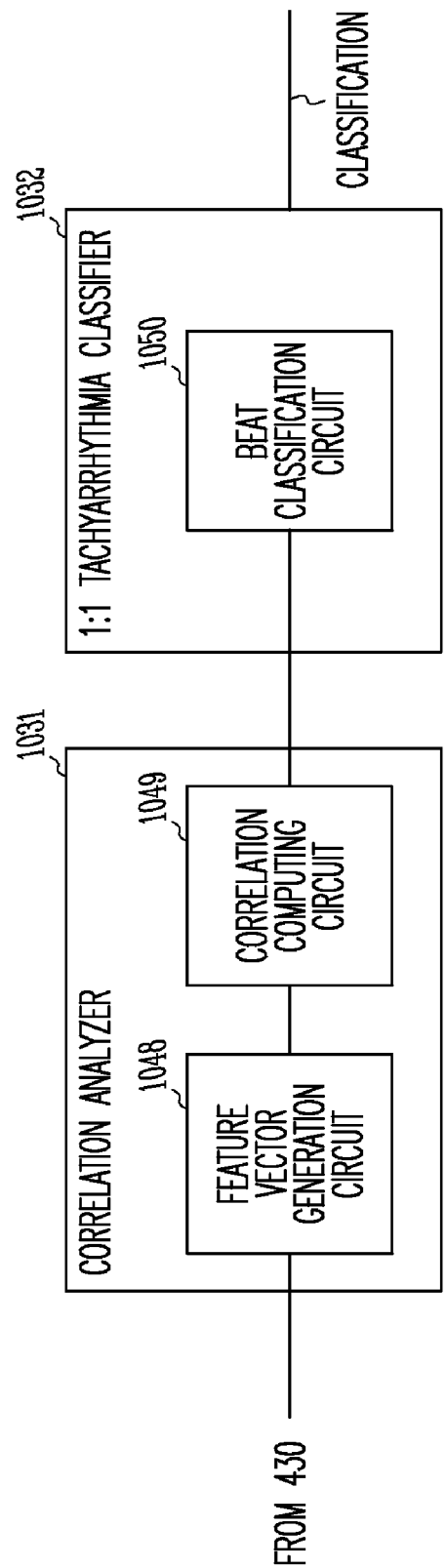
FIG. 10 is a block diagram illustrating an embodiment of a correlation analyzer and a 1:1 tachyarrhythmia classifier being part of the morphology-based 1:1 tachyarrhythmia discrimination circuit.

FIG. 10 is a block diagram illustrating an embodiment of a correlation analyzer 1031 and a 1:1 tachyarrhythmia classifier 1032. Correlation analyzer 1031 is an embodiment of correlation analyzer 431, and 1:1 tachyarrhythmia classifier 1032 is an embodiment of 1:1 tachyarrhythmia classifier 432. Correlation analyzer 1031 includes a feature vector generation circuit 1048 and a correlation computing circuit 1049, and 1:1 tachyarrhythmia classifier 1032 includes a beat classification circuit 1050.

Feature vector generation circuit 1048 produces a template feature vector ($\underline{a}$), an arrhythmic feature vector ($\underline{b}$), a maximum feature vector ($\underline{a}_{max}$), and a minimum feature vector ($\underline{a}_{min}$). The template feature vector ($\underline{a}$) is associated with a plurality of template morphological features of a plurality of template heart beats of a known type cardiac rhythm. The arrhythmic feature vector ($\underline{b}$) is associated with a plurality of arrhythmic morphological features of an arrhythmic heart beat of a 1:1 tachyarrhythmia. The maximum feature vector ($\underline{a}_{max}$) and the minimum feature vector ($\underline{a}_{min}$) are each the sum of the template feature vector ($\underline{a}$) and a deviation vector, and are produced based on the template morphological features and the arrhythmic morphological features. Each deviation vector is a measure of beat-to-beat morphological variations in the plurality of template heart beats. Correlation computing circuit 1049 computes a mean feature correlation coefficient ($Fcc_{mean}$) based on the template feature vector ($\underline{a}$) and the arrhythmic feature vector ($\underline{b}$), a maximum feature correlation coefficient ($Fcc_{max}$) based on the maximum feature vector ($\underline{a}_{max}$) and the arrhythmic feature vector ($\underline{b}$), and a minimum feature correlation coefficient ($Fcc_{min}$) based on the minimum feature vector ($\underline{a}_{min}$) and the arrhythmic feature vector ($\underline{b}$). Beat classification circuit 1050 classifies the arrhythmic heart beat based on the mean feature correlation coefficient ($Fcc_{mean}$), the maximum feature correlation coefficient ($Fcc_{max}$), the minimum feature correlation coefficient ($Fcc_{min}$), and at least one predetermined correlation threshold.

Figure 11:
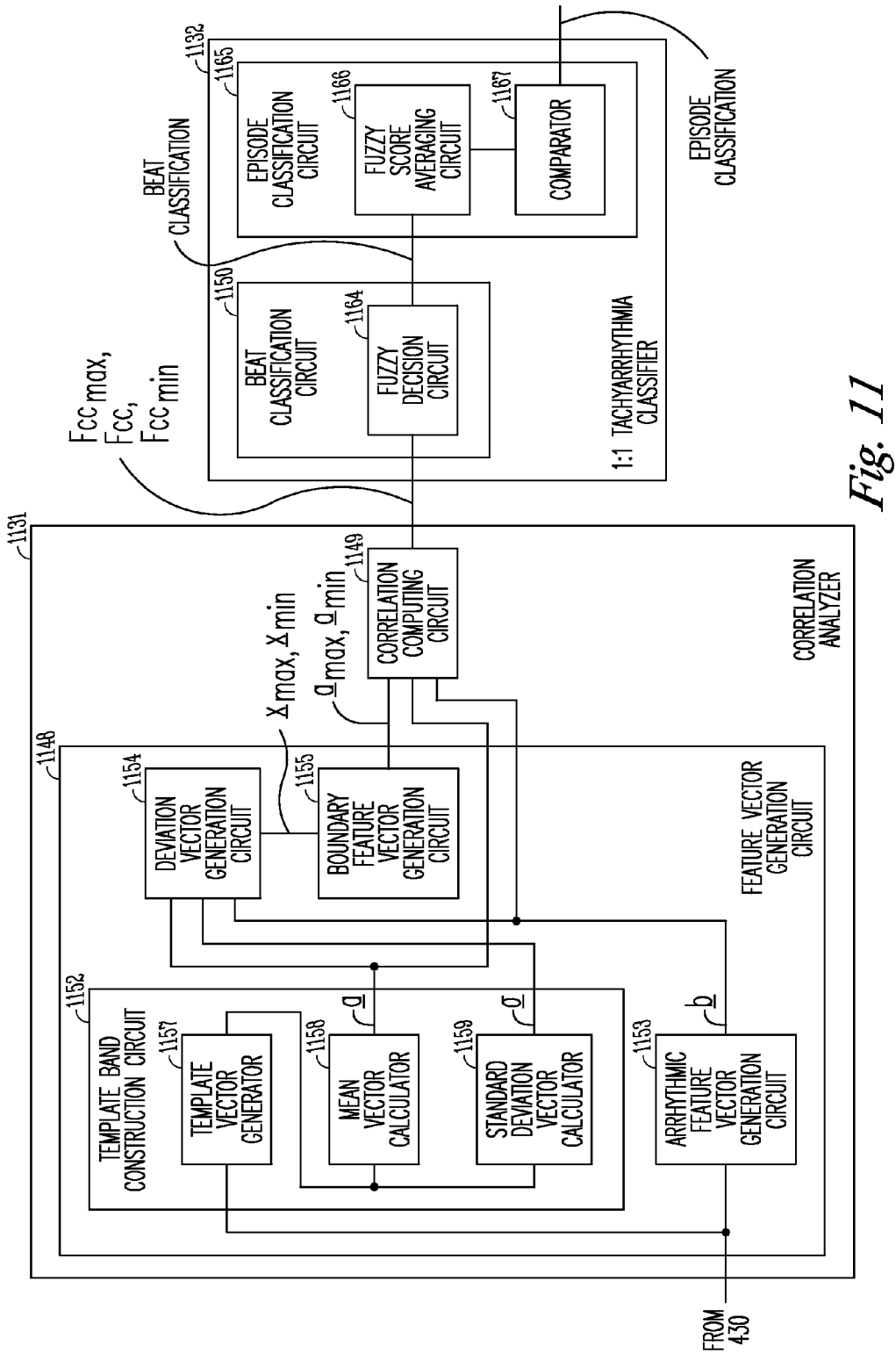
FIG. 11 is a block diagram illustrating a specific embodiment of the correlation analyzer and the 1:1 tachyarrhythmia classifier of FIG. 10.

FIG. 11 is a block diagram illustrating a correlation analyzer 1131, which is a specific embodiment of correlation analyzer 1031, and a 1:1 tachyarrhythmia classifier 1132, which is a specific embodiment of 1:1 tachyarrhythmia classifier 1032. Correlation analyzer 1131 includes a feature vector generation circuit 1148 and a correlation computing circuit 1149, and 1:1 tachyarrhythmia classifier 1132 includes a beat classification circuit 1150 and an episode classification circuit 1165.

Feature vector generation circuit 1148 is a specific embodiment of feature vector generation circuit 1048 and includes a template band construction circuit 1152, an arrhythmic feature vector generation circuit 1153, a deviation vector generation circuit 1154, and a boundary feature vector generation circuit 1155. Template band construction circuit 1152 produces the template feature vector ($\underline{a}$) and a template standard deviation vector ($\underline{\sigma}$) based on the morphological features of the plurality of template heart beats. Template band construction circuit 1152 includes a template vector generator 1157, a mean vector calculator 1158, and a standard deviation vector calculator 1159. Template vector generator 1157 produces a plurality of template feature vectors each representative of a plurality of template morphological features of one template heart beat of the plurality of template heart beats. Mean vector calculator 1158 produces the template feature vector ($\underline{a}$), which is a mean vector of the plurality of template feature vectors. Standard deviation vector calculator 1159 produces the template standard deviation vector ($\underline{\sigma}$), which is a standard deviation vector of the plurality of template feature vectors. Arrhythmic feature vector generation circuit 1153 produces the arrhythmic feature vector ($\underline{b}$) based on the morphological features of the arrhythmic heart beat of the 1:1 tachyarrhythmia. Deviation vector generation circuit 1154 produces a maximum deviation vector ($\underline{x}_{max}$) and a minimum deviation vector ($\underline{x}_{min}$) based on the template feature vector ($\underline{a}$), the arrhythmic feature vector ($\underline{b}$), and the template standard deviation vector ($\underline{\sigma}$). In one embodiment, the maximum deviation vector ($\underline{x}_{max}$) and a minimum deviation vector ($\underline{x}_{min}$) are calculated based on:

$$\underline{x}_{max} = \frac{\underline{b} - \underline{a}}{\|\underline{b} - \underline{a}\|_\infty} \cdot * \underline{\delta}, \text{ and} \quad [1]$$

$$\underline{x}_{min} = \frac{\underline{b} - \underline{a}}{\|\underline{b} - \underline{a}\|_\infty} \cdot * \underline{\delta}, \quad [2]$$

where $\underline{\delta}$ is a feature variation vector ($\underline{\delta}=k\underline{\sigma}$, where k is a scalar constant dependent on the desired confidence level), $\|\ \|_\infty$ is the maximum of the absolute value, and "*" is the operator for an element-by-element product. Boundary feature vector generation circuit 1155 produces the maximum feature vector ($\underline{a}_{max}$) by adding the maximum deviation vector ($\underline{x}_{max}$) to the template feature vector ($\underline{a}$) and produces the minimum feature vector ($\underline{a}_{min}$) by adding the minimum deviation vector ($\underline{x}_{min}$) to the template feature vector ($\underline{a}$). That is:

$$\underline{a}_{max} = \underline{a} + \underline{x}_{max}, \text{ and} \quad [3]$$

$$\underline{a}_{min} = \underline{a} + \underline{x}_{min}. \quad [4]$$

Correlation computing circuit 1149 is a specific embodiment of correlation computing circuit 1049 and computes feature correlation coefficients including a mean feature correlation coefficient ($Fcc_{mean}$), a maximum feature correlation coefficient ($Fcc_{max}$), and a minimum feature correlation coefficient ($Fcc_{min}$). In one embodiment, as discussed in U.S. Pat.

No. 6,708,058, a feature correlation coefficient is computed using the following equation:

$$Fcc = FCC(\underline{a}, \underline{b}) \quad [5]$$

$$= \frac{\left(N\sum_{i=1}^{N} a_i b_i - \left(\sum_{i=1}^{N} a_i\right)\left(\sum_{i=1}^{N} b_i\right)\right)^2}{\left(N\sum_{i=1}^{N} a_i^2 - \left(\sum_{i=1}^{N} a_i\right)^2\right)\left(N\sum_{i=1}^{N} b_i^2 - \left(\sum_{i=1}^{N} b_i\right)^2\right)},$$

where N is the number of morphological features extracted from each template or arrhythmic heart beat, $a_i$ is associated with the $i^{th}$ template morphological feature, and $b_i$ is associated with the $i^{th}$ arrhythmic morphological feature. In one specific example, N=8. Correlation computing circuit 1149 computes feature correlation coefficients using the following equations:

$$Fcc_{mean} = FCC(\underline{a}, \underline{b}), \quad [6]$$

$$Fcc_{max} = FCC(\underline{a}_{max}, \underline{b}), \quad [7]$$

$$Fcc_{min} = FCC(\underline{a}_{min}, \underline{b}), \quad [8]$$

Beat classification circuit 1150 is a specific embodiment of beat classification circuit 1050 and include a fuzzy decision circuit 1164. Fuzzy decision circuit 1164 calculate a fuzzy score for the arrhythmic heart beat based on the mean feature correlation coefficient ($Fcc_{mean}$), the maximum feature correlation coefficient ($Fcc_{max}$), the minimum feature correlation coefficient ($Fcc_{min}$), and the at least one predetermined correlation threshold ($Fcc_{th}$). The fuzzy score represents an estimated probability of the 1:1 tachyarrhythmia being a known type tachyarrhythmia. Additional details of the fuzzy score calculation is discussed below with reference to FIG. 14.

Episode classification circuit 1165 classifies the 1:1 tachyarrhythmia based on the fuzzy scores produced for a plurality of arrhythmic heart beats of the 1:1 tachyarrhythmia. The plurality of arrhythmic heart beats represent an "episode" of the 1:1 tachyarrhythmia. Episode classification circuit 1165 includes a fuzzy score averaging circuit 1166 and a comparator 1167. Fuzzy score averaging circuit 1166 calculates an episode fuzzy score being an average of the fuzzy scores produced by correlation computing circuit 1149 for the plurality of arrhythmic heart beats. Comparator 1167 compares the episode fuzzy score to a predetermined classification threshold and classifies the 1:1 tachyarrhythmia based on an outcome of the comparison. In one embodiment, comparator 1167 classifies the 1:1 tachyarrhythmia as a known first type tachyarrhythmia if the episode fuzzy score exceeds the predetermined classification threshold and a known second type tachyarrhythmia if the episode fuzzy score does not exceed the predetermined classification threshold.

Figure 12:
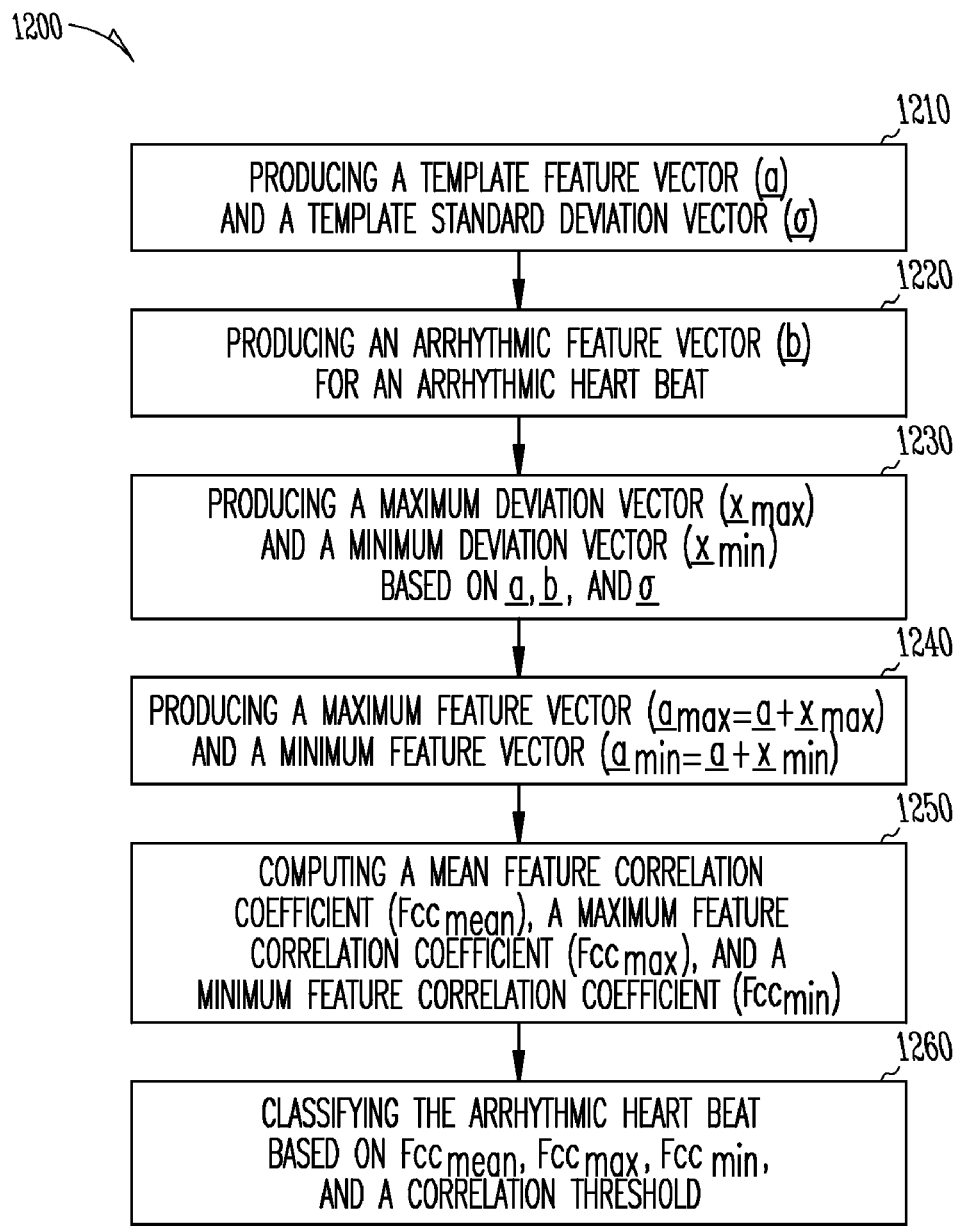
FIG. 12 is a flow chart illustrating an embodiment of a method for analyzing correlation and classifying 1:1 tachyarrhythmias for the morphology-based 1:1 tachyarrhythmia discrimination.

FIG. 12 is a flow chart illustrating an embodiment of a method 1200 for analyzing correlation and classifying 1:1 tachyarrhythmias for the morphology-based 1:1 tachyarrhythmia discrimination. In one embodiment, correlation analyzer 1031 and 1:1 tachyarrhythmia classifier 1032, including their specific embodiment, correlation analyzer 1131 and 1:1 tachyarrhythmia classifier 1132, perform method 1200.

A template feature vector (a) and a template standard deviation vector ($\sigma$) are produced based on morphological features of a plurality of template heart beats of a known type cardiac rhythm at 1210. In one embodiment, a plurality of template feature vectors each representative of a plurality of template morphological features of one of the template heart beats are received. The template feature vector (a) is a mean vector of the plurality of template feature vectors. The template standard deviation vector ($\sigma$) is a standard deviation vector of the plurality of template feature vectors.

An arrhythmic feature vector (b) is produced based on morphological features of an arrhythmic heart beat of a 1:1 tachyarrhythmia at 1220. In one embodiment, an arrhythmic waveform representing a heart beat of the 1:1 tachyarrhythmia is received. A plurality of morphological features are extracted from the arrhythmic waveform. The arrhythmic feature vector (b) is associated with the plurality of morphological features.

A maximum deviation vector ($x_{max}$) and a minimum deviation vector ($x_{min}$) are produced based on the template feature vector (a), the arrhythmic feature vector (b), and the template standard deviation vector ($\sigma$), using equations [1] and [2], at 1230. A maximum feature vector ($a_{max}$) and a minimum feature vector ($a_{min}$) are produced at 1240. The maximum feature vector ($a_{max}$) is calculated by adding the maximum deviation vector ($x_{max}$) to the template feature vector (a), i.e., using equation [3]. The minimum feature vector ($a_{min}$) is calculated by adding the minimum deviation vector ($x_{min}$) to the template feature vector (a), i.e., using equation [4].

A mean feature correlation coefficient ($Fcc_{mean}$), a maximum feature correlation coefficient ($Fcc_{max}$), and a minimum feature correlation coefficient ($Fcc_{min}$) are computed at 1250. The maximum feature correlation coefficient ($Fcc_{max}$) is computed based on the maximum feature vector ($a_{max}$) and the arrhythmic feature vector (b) using equation [6]. The a mean feature correlation coefficient ($Fcc_{mean}$) is computed based on the template feature vector (a) and the arrhythmic feature vector (b) using equation [7]. The minimum feature correlation coefficient ($Fcc_{min}$) is computed based on the minimum feature vector ($a_{min}$) and the arrhythmic feature vector (b) using equation [8].

The arrhythmic heart beat is classified based on the mean feature correlation coefficient ($Fcc_{mean}$), the maximum feature correlation coefficient ($Fcc_{max}$), the minimum feature correlation coefficient ($Fcc_{min}$), and at least one predetermined correlation threshold ($Fcc_{th}$) at 1260. In one embodiment, a fuzzy score for the arrhythmic heart beat is calculated based on based on the mean feature correlation coefficient ($Fcc_{mean}$), the maximum feature correlation coefficient ($Fcc_{max}$), the minimum feature correlation coefficient ($Fcc_{min}$), and the predetermined correlation threshold ($Fcc_{th}$). The fuzzy score represents an estimated probability of the 1:1 tachyarrhythmia being a known type tachyarrhythmia.

In a further embodiment, the 1:1 tachyarrhythmia is classified based on the fuzzy scores produced for a plurality of arrhythmic heart beats of the 1:1 tachyarrhythmia. An episode fuzzy score is calculated by averaging the fuzzy scores produced for the plurality of arrhythmic heart beats and is compared to a predetermined classification threshold. The 1:1 tachyarrhythmia is classified as a known first type tachyarrhythmia if the episode fuzzy score exceeds the predetermined classification threshold and as a known second type tachyarrhythmia if the episode fuzzy score does not exceed the predetermined classification threshold. In one specific example, the known type cardiac rhythm is an NSR, the known first type tachyarrhythmia is an SVT, and the known second type tachyarrhythmia is a VT.

Figure 13:
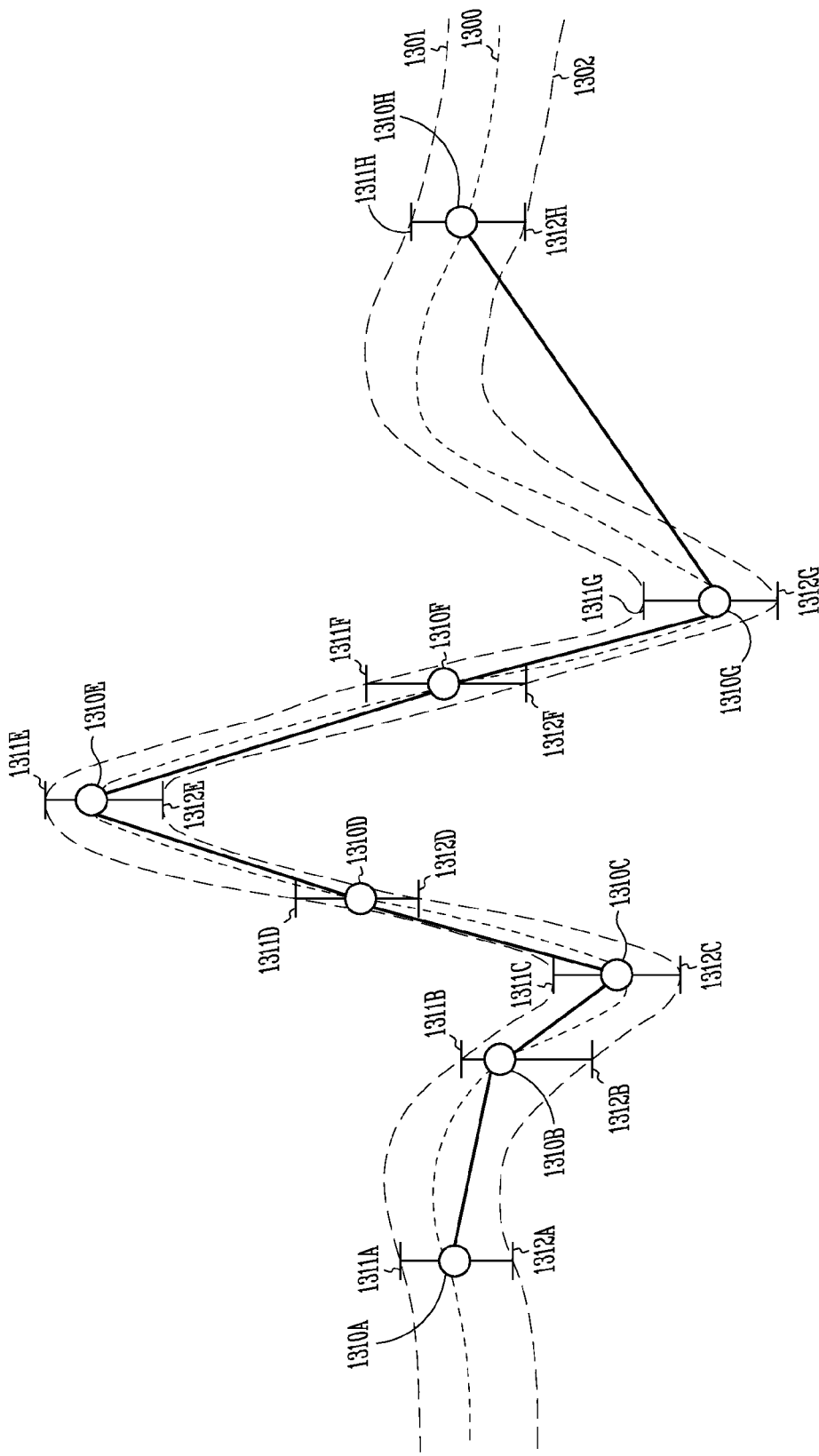
FIG. 13 is a graph illustrating an exemplary template band as used in the method of FIG. 12.

FIG. 13 is a graph illustrating an exemplary template band as used in method 1200. As illustrated, the template band includes a mean waveform 1300 with two curves 1301 and 1302 representing the confidence levels (a+$\delta$ and a−$\delta$). Each morphological feature is associated with a mean point being one of points 1310A-H and a range between a maximum point being one of points 1311A-H and a minimum point being one of points 1312A-H. The mean feature vector (a) is associated with points 1310A-1310H on mean waveform 1300. The maximum feature vector ($a_{max}$) and the minimum feature vector $a_{min}$) are within the template band.

Figure 14A:
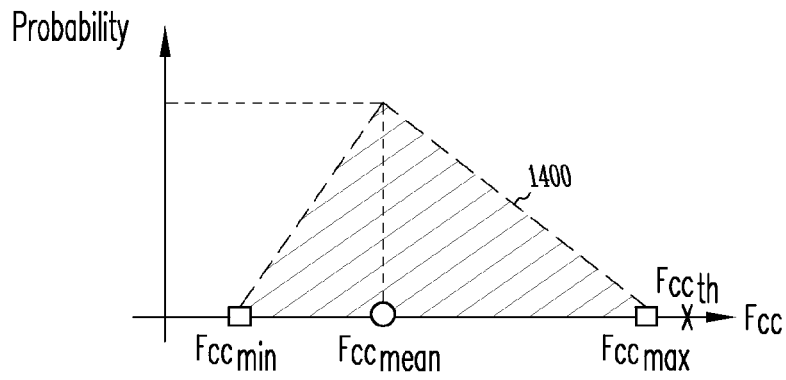
FIGS. 14A-D include graphs illustrating a fuzzy decisional process in classifying 1:1 tachyarrhythmias for the method of FIG. 12.
Figure 14B:
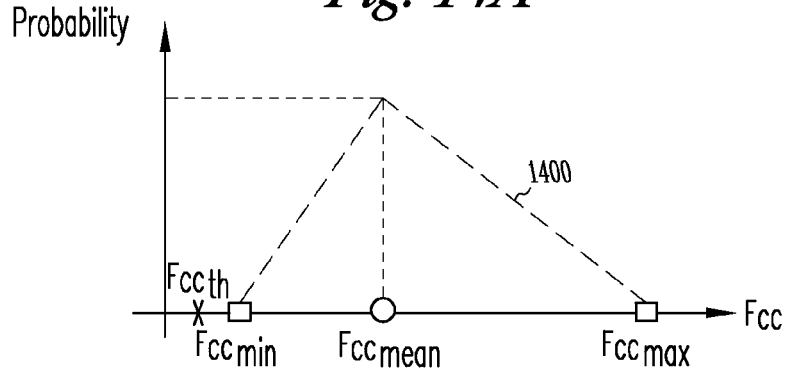
Figure 14C:
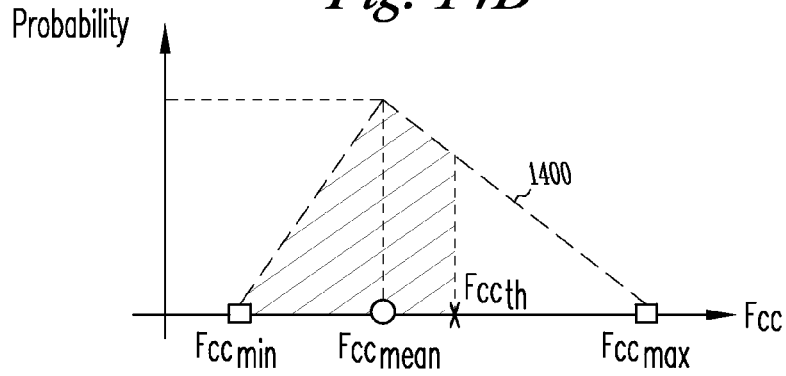

FIGS. 14A-D include graphs illustrating a fuzzy decisional process for classifying the arrhythmia beat in step 1260 of method 1200. A curve 1400 represents an estimate of the distribution of the probability that a detected 1:1 tachyarrhythmia is of a particular type over the feature correlation coefficient. As illustrated, the probability distributes between the maximum feature correlation coefficient ($Fcc_{max}$) and the minimum feature correlation coefficient ($Fcc_{min}$), and peaks at the mean feature correlation coefficient ($Fcc_{mean}$). The fuzzy score is the ratio of the shaded area to the area of the triangle between the estimated probability distribution curve and the Fcc axis. FIG. 14A illustrates the scenario that the predetermined correlation threshold ($Fcc_{th}$) is greater than the maximum feature correlation coefficient ($Fcc_{max}$). The corresponding fuzzy score is 1. FIG. 14B illustrates the scenario that the predetermined correlation threshold ($Fcc_{th}$) is smaller than the minimum feature correlation coefficient ($Fcc_{min}$). The corresponding fuzzy score is 0. FIG. 14C illustrates the scenario that the predetermined correlation threshold ($Fcc_{th}$) is between the mean feature correlation coefficient ($Fcc_{mean}$) and the maximum feature correlation coefficient ($Fcc_{max}$). The corresponding fuzzy score is given as:

$$\text{fuzzy\_score} = 1 - \frac{(Fcc_{max} - Fcc_{th})^2}{(Fcc_{max} - Fcc_{mean}) \cdot (Fcc_{max} - Fcc_{min})}. \quad [9]$$

Figure 14D:
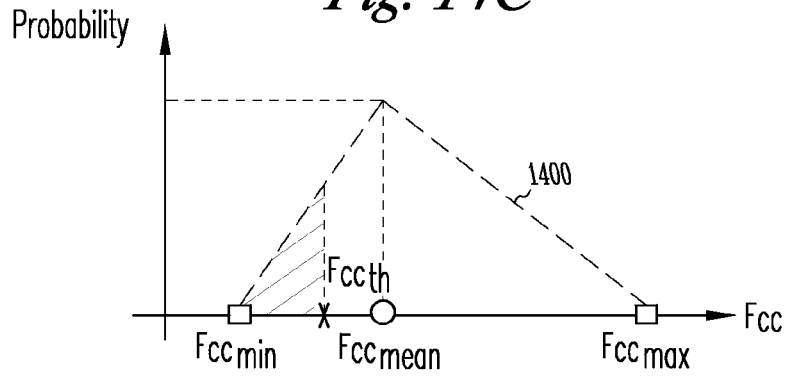

FIG. 14D illustrates the scenario that the predetermined correlation threshold ($Fcc_{th}$) is between the minimum feature correlation coefficient ($Fcc_{min}$) and the mean feature correlation coefficient ($Fcc_{mean}$). The corresponding fuzzy score is given as:

$$\text{fuzzy\_score} = \frac{(Fcc_{th} - Fcc_{min})^2}{(Fcc_{mean} - Fcc_{min}) \cdot (Fcc_{max} - Fcc_{min})}. \quad [10]$$

If the fuzzy score is 1, the arrhythmic heart beat is classified as a known first type tachyarrhythmia. If the fuzzy score is 0, the arrhythmic heart beat is classified as a known second type tachyarrhythmia. If the fuzzy score is between 0 and 1, the fuzzy score indicates the probability that the arrhythmic heart beat is the known first type tachyarrhythmia, and the arrhythmic heart beat is classified by giving the probability. In one specific example, the known type cardiac rhythm is an NSR, the known first type tachyarrhythmia is a VT, and the known second type tachyarrhythmia is an SVT.

Figure 15:
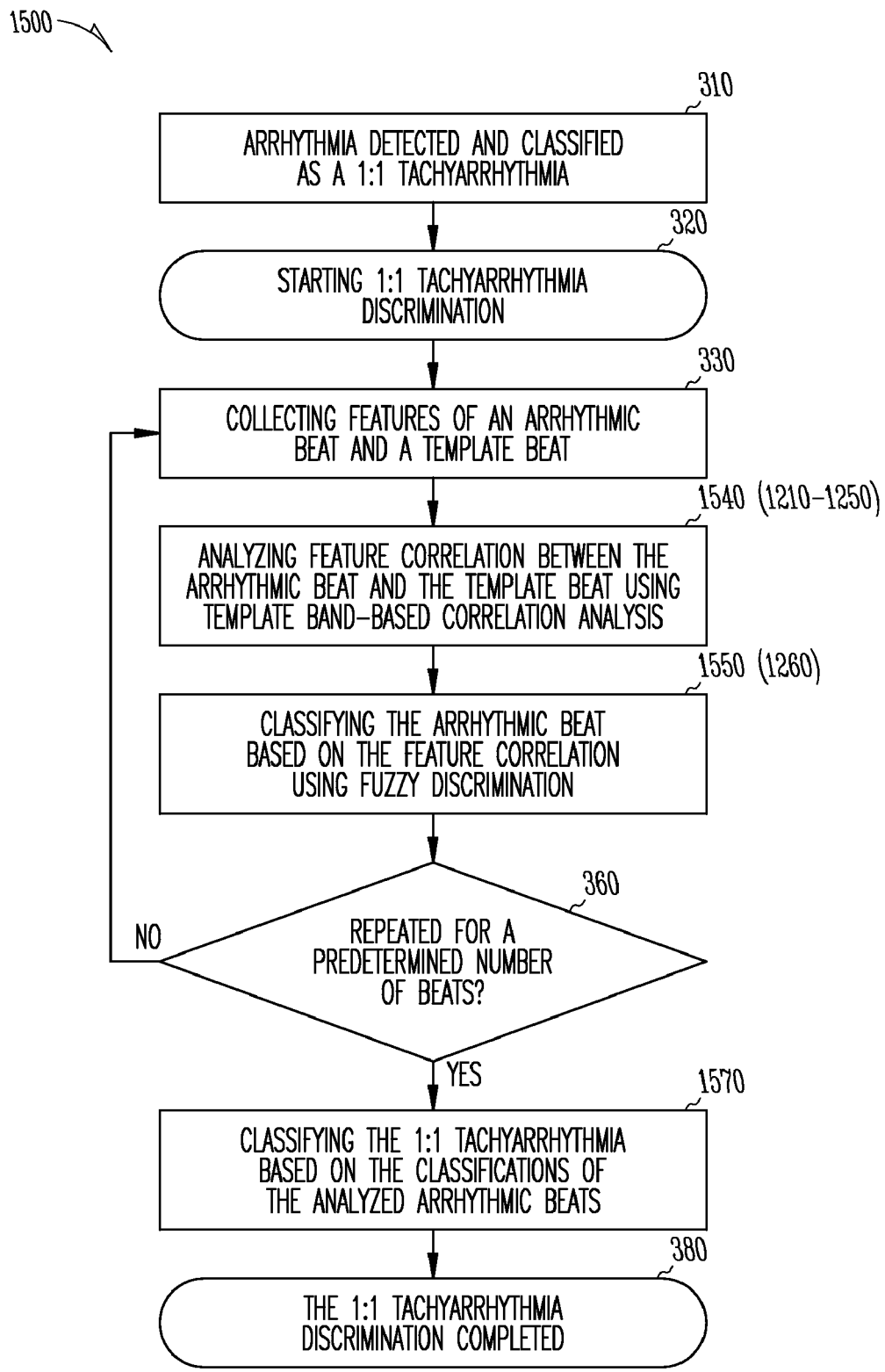
FIG. 15 is a flow chart illustrating a specific embodiment of the method for morphology-based 1:1 tachyarrhythmia discrimination as illustrated in FIG. 3 including an exemplary application of the method of FIG. 12.

FIG. 15 is a flow chart illustrating a method 1500 for the morphology-based tachyarrhythmia discrimination. Method 1500 is another specific embodiment of method 300 and includes an exemplary application of method 1200. Step 1540 in method 1500 is a specific embodiment of step 340 and includes steps 1210-1250 of method 1200 as discussed above. Step 1550 in method 1500 is a specific embodiment of step 350 and includes step 1260 of method 1200 as discussed above. Step 1570 in method 1500 is a specific embodiment of step 370. At 1570, the 1:1 tachyarrhythmia is classified based on fuzzy scores calculated for a plurality of arrhythmic heart beats sensed during the 1:1 tachyarrhythmia. In one embodiment, the fuzzy scores are averaged and compared to a predetermined classification threshold. The 1:1 tachyarrhythmia is classified based on the outcome of the comparison.

Because of the variations in the morphology associated with a heart beat of a known rhythm such as the NSR, an averaged waveform does not always provide an unbiased template for the morphology-based tachyarrhythmia discrimination. Correlation analysis and tachyarrhythmia classification using method 1200 in a morphology-based tachyarrhythmia discrimination method such as method 300 takes into account the variation and uncertainty of a template waveform. The fuzzy score reflects such variation and uncertainty. The classification of a 1:1 tachyarrhythmia using the episode fuzzy score can be conceptualized as being advantageously based on a value fusion rather than a decision fusion.

Mahalanobis Distance-Based Correlation Analysis

Figure 16:
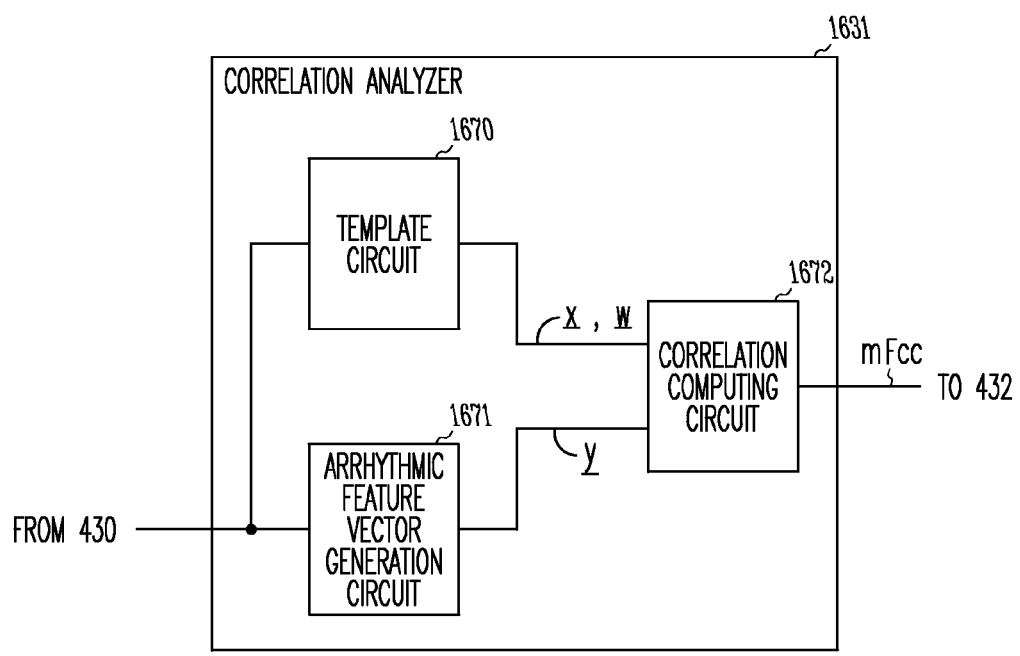
FIG. 16 is a block diagram illustrating an embodiment of another correlation analyzer being part of the morphology-based 1:1 tachyarrhythmia discrimination circuit.

FIG. 16 is a block diagram illustrating an embodiment of a correlation analyzer 1631. Correlation analyzer 1631 is another embodiment of correlation analyzer 431 and includes a template circuit 1670, an arrhythmic feature vector generation circuit 1671, and a correlation computing circuit 1672. Correlation analyzer 1631 performs a Mahalanobis distance-based correlation analysis between an arrhythmic waveform and a template waveform.

Template circuit 1670 produces a template feature vector (x) and an inverse covariance matrix (W) of a template feature matrix (X) based on a plurality of template heart beats of a known type cardiac rhythm. Each template heart beat is represented by a template waveform including a plurality of template morphological features. The template feature vector (x), the template feature matrix (X), and the inverse covariance matrix (W) are each produced based on the template morphological features of the plurality of template heart beats. Arrhythmic feature vector generation circuit 1671 produces an arrhythmic feature vector (y) based on a plurality of arrhythmic morphological features associated with an arrhythmic heart beat of a 1:1 tachyarrhythmia. Correlation computing circuit 1672 produces a Mahalanobis distance-based feature correlation coefficient (mFcc) for the arrhythmic heart beat based on the template feature vector (x), the arrhythmic feature vector (y), and the inverse covariance matrix (W). The Mahalanobis distance-based feature correlation coefficient (mFcc) is computed based on equation [11]:

$$mFcc = \frac{(y^T \underline{W} x)^2}{y^T \underline{W} y \cdot x^T \underline{W} x}, \quad [11]$$

where $x^T$ is the transposed x, and $y^T$ is the transposed y.

Figure 17:
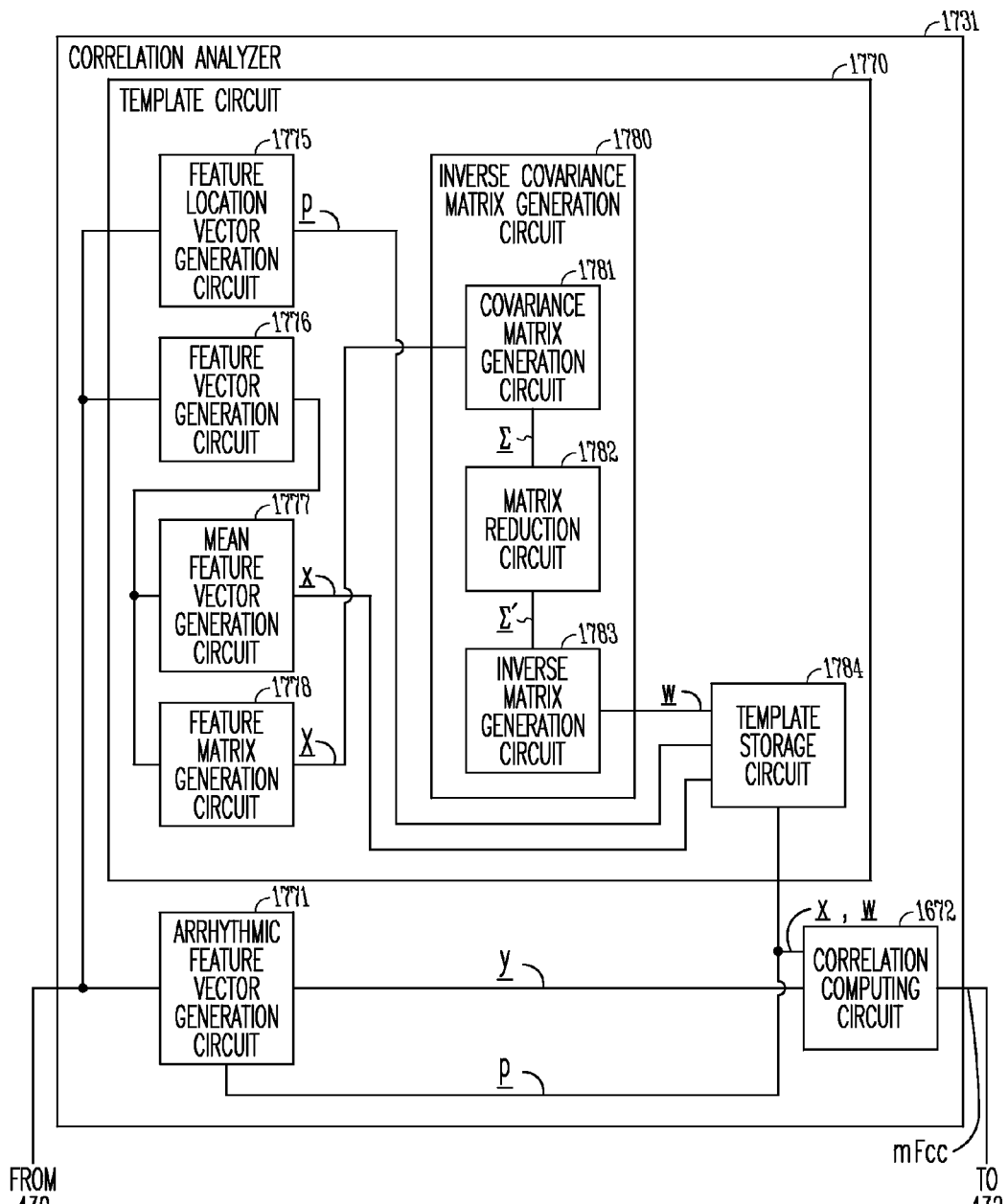
FIG. 17 is a block diagram illustrating a specific embodiment of the correlation analyzer of FIG. 16.

FIG. 17 is a block diagram illustrating an embodiment of a correlation analyzer 1731, which is a specific embodiment of correlation analyzer 1631. Correlation analyzer 1731 includes a template circuit 1770, an arrhythmic feature vector generation circuit 1771, and correlation computing circuit 1672.

Template circuit 1770 is a specific embodiment of template circuit 1670 and includes a feature location vector generation circuit 1775, a feature vector generation circuit 1776, a mean feature vector generation circuit 1777, a feature matrix generation circuit 1778, an inverse covariance matrix generation circuit 1780, and a template storage circuit 1784. Feature location vector generation circuit 1775 produce a feature location vector (p) indicative of the locations of template morphological features associated with each of the plurality of template heart beats. Feature vector generation circuit 1776 produces a feature vector for each of the plurality of template heart beats. The feature vector includes parameters measured from a plurality of template morphological features located for that template heart beat. Mean feature vector generation circuit 1777 produces the template feature vector ($\underline{x}$) as the mean vector of the feature vectors produced for the plurality of template heart beats. Feature matrix generation circuit 1778 produces the template feature matrix ($\underline{X}$) including all the feature vectors produced for the plurality of template heart beats. That is:

$$X = \begin{bmatrix} x_{11} & x_{12} & \cdots & x_{1N} \\ x_{21} & x_{22} & \cdots & x_{2N} \\ \vdots & \vdots & \ddots & \vdots \\ x_{M1} & x_{m2} & \cdots & x_{MN} \end{bmatrix}, \quad [12]$$

where N is the number of template heart beats in the plurality of template heart beats and M is the number of the template morphological features associated with each template heart beat of the plurality of template heart beats.

Inverse covariance matrix generation circuit 1780 computes the inverse covariance matrix ($\underline{W}$) of the template feature matrix ($\underline{X}$). Inverse covariance matrix generation circuit 1780 includes a covariance matrix generation circuit 1781, a matrix reduction circuit 1782, and an inverse matrix generation circuit 1783. Covariance matrix generation circuit 1781 computes a covariance matrix ($\Sigma$) of the template feature matrix ($\underline{X}$) based on equation [13]:

$$\Sigma = \begin{bmatrix} \sigma_1^2 & \sigma_{12}^2 & \cdots & \sigma_{1M}^2 \\ \sigma_{21}^2 & \sigma_2^2 & \cdots & \sigma_{2M}^2 \\ \vdots & \vdots & \ddots & \vdots \\ \sigma_{M1}^2 & \sigma_{M2}^2 & \cdots & \sigma_M^2 \end{bmatrix}, \quad [13]$$

where $\sigma_i^2$ is the variance of the $i^{th}$ template morphological feature, and $\sigma_{ij}^2$ is the covariance of between the $i^{th}$ template morphological feature and the $j^{th}$ template morphological feature. Matrix reduction circuit 1782 produces a reduced covariance matrix ($\Sigma'$) by setting all non-diagonal elements of the covariance matrix ($\Sigma$) to zero. That is:

$$\Sigma' = \begin{bmatrix} \sigma_1^2 & 0 & \cdots & 0 \\ 0 & \sigma_2^2 & \cdots & 0 \\ \vdots & \vdots & \ddots & \vdots \\ 0 & 0 & \cdots & \sigma_N^2 \end{bmatrix}. \quad [14]$$

Inverse matrix generation circuit 1783 produces the inverse covariance matrix ($\underline{W}$) being an inverse covariance matrix of the reduced covariance matrix ($\Sigma'$). That is:

$$\underline{W} = \begin{bmatrix} \frac{1}{\sigma_1^2 + \delta} & 0 & \cdots & 0 \\ 0 & \frac{1}{\sigma_2^2 + \delta} & \cdots & 0 \\ \vdots & \vdots & \ddots & \vdots \\ 0 & 0 & \cdots & \frac{1}{\sigma_N^2 + \delta} \end{bmatrix}, \quad [15]$$

where $\delta$ is a small regularization factor added to prevent the inverse covariance matrix ($\underline{W}$) from being singular. In one specific embodiment, $\delta$ is set to one half of the smallest $\sigma_i^2$.

Template storage circuit 1784 stores the template feature vector ($\underline{x}$), the feature location vector ($\underline{p}$), and the inverse covariance matrix ($\underline{W}$) for the correlation analysis when a tachyarrhythmia is detected and classified as a 1:1 tachyarrhythmia.

Arrhythmic feature vector generation circuit 1771 is a specific embodiment of arrhythmic feature vector generation circuit 1671 and includes a feature input and a feature extraction circuit. The feature input receives an arrhythmic waveform representative of the arrhythmic heart beat of the 1:1 tachyarrhythmia. The feature extraction circuit extracts a plurality of arrhythmic morphological features form that arrhythmic waveform based on the feature location vector ($\underline{p}$) and produces the arrhythmic feature vector ($\underline{y}$).

Figure 18:
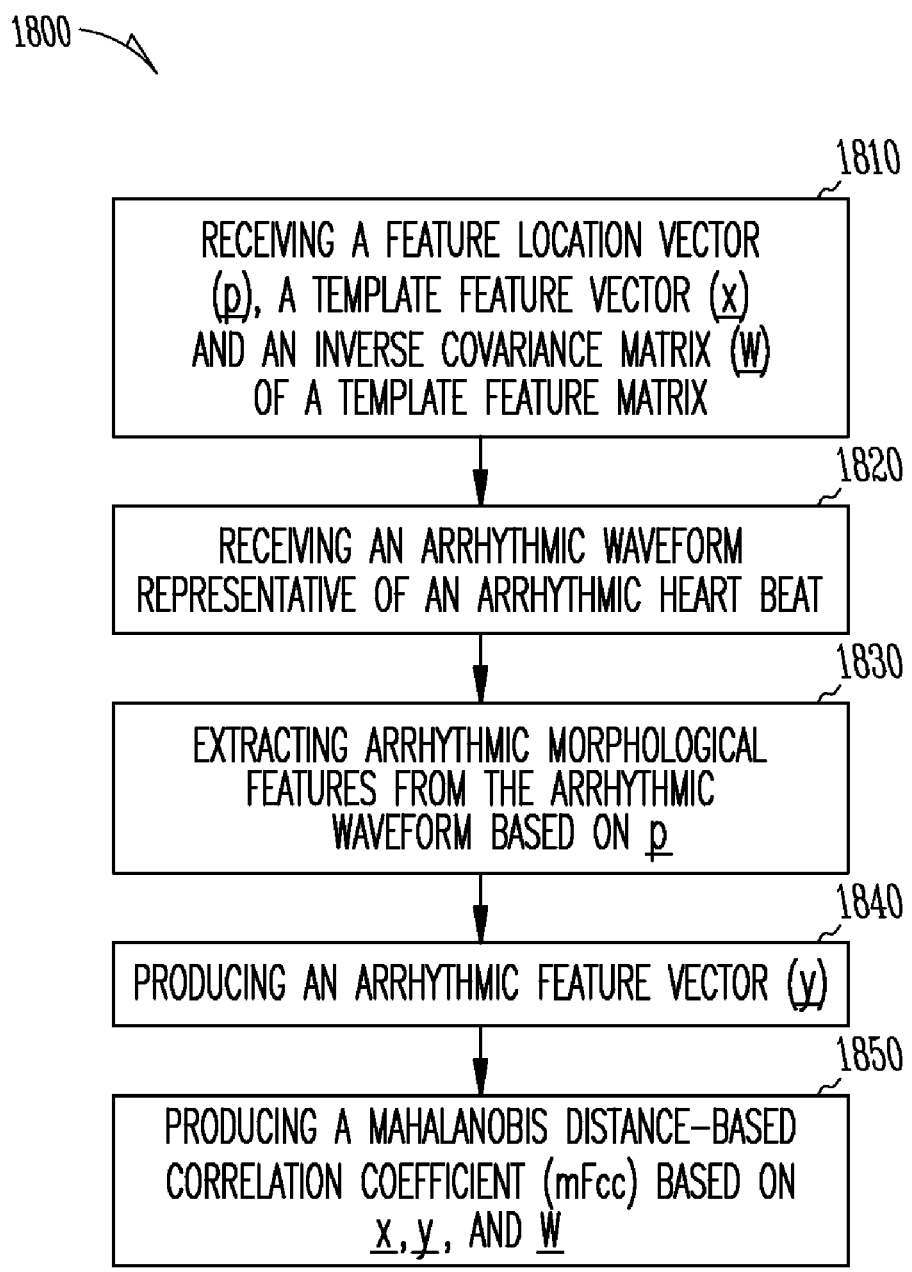
FIG. 18 is a flow chart illustrating an embodiment of another method for analyzing correlation for the morphology-based 1:1 tachyarrhythmia discrimination.

FIG. 18 is a flow chart illustrating an embodiment of a method 1800 for analyzing correlation for the morphology-based 1:1 tachyarrhythmia discrimination. In one embodiment, method 1800 is performed by correlation analyzer 1631, including its specific embodiment, correlation analyzer 1731.

A feature location vector ($\underline{p}$), a template feature vector ($\underline{x}$), and an inverse covariance matrix ($\underline{W}$) of a template feature matrix are received at 1810. These vectors and matrix are associated with a plurality of template heart beats of a known type cardiac rhythm. In one embodiment, the known type cardiac rhythm includes an NSR. Each template heart beat is represented by a template waveform having a plurality of template morphological features. In one embodiment, a plurality of template morphological features are located for each template heart beat. The feature location vector ($\underline{p}$) is produced to indicate the locations of the template morphological features for all the template heart beats. A feature vector is produced for each template heart beat based on the template morphological features located for that template heart beat. A template feature vector ($\underline{x}$) is produced as the mean vector of all the feature vectors produced for the plurality of template heart beats. A template feature matrix ($\underline{X}$) is produced to include all the feature vectors produced, as shown in equation [12]. A covariance matrix ($\Sigma$) of the template feature matrix ($\underline{X}$) is computed using equation [13]. A reduced covariance matrix ($\Sigma'$) is produced by setting all non-diagonal elements of the covariance matrix ($\Sigma$) to zero, as shown in equation [14]. The inverse covariance matrix ($\underline{W}$) is produced as an inverse covariance matrix of the reduced covariance matrix ($\Sigma'$), as shown in equation [15]. After being produced, at least the template feature vector ($\underline{x}$), the feature location vector ($\underline{p}$), and the inverse covariance matrix ($\underline{W}$) are stored for use in the Mahalanobis distance-based correlation analysis when a 1:1 tachyarrhythmia is detected.

An arrhythmic waveform representative of an arrhythmic heart beat of a 1:1 tachyarrhythmia is received at 1820. A plurality of arrhythmic morphological features are extracted from the arrhythmic waveform based on at least the feature location vector ($\underline{p}$) at 1830. An arrhythmic feature vector ($\underline{y}$) associated with the arrhythmic heart beat is produced at 1840. A Mahalanobis distance-based correlation coefficient (mFcc) for the each arrhythmic heart beat is produced based on the template feature vector ($\underline{b}$), the arrhythmic feature vector ($\underline{y}$), and the inverse covariance matrix ($\underline{W}$), using equation [11], at 1850.

Figure 19:
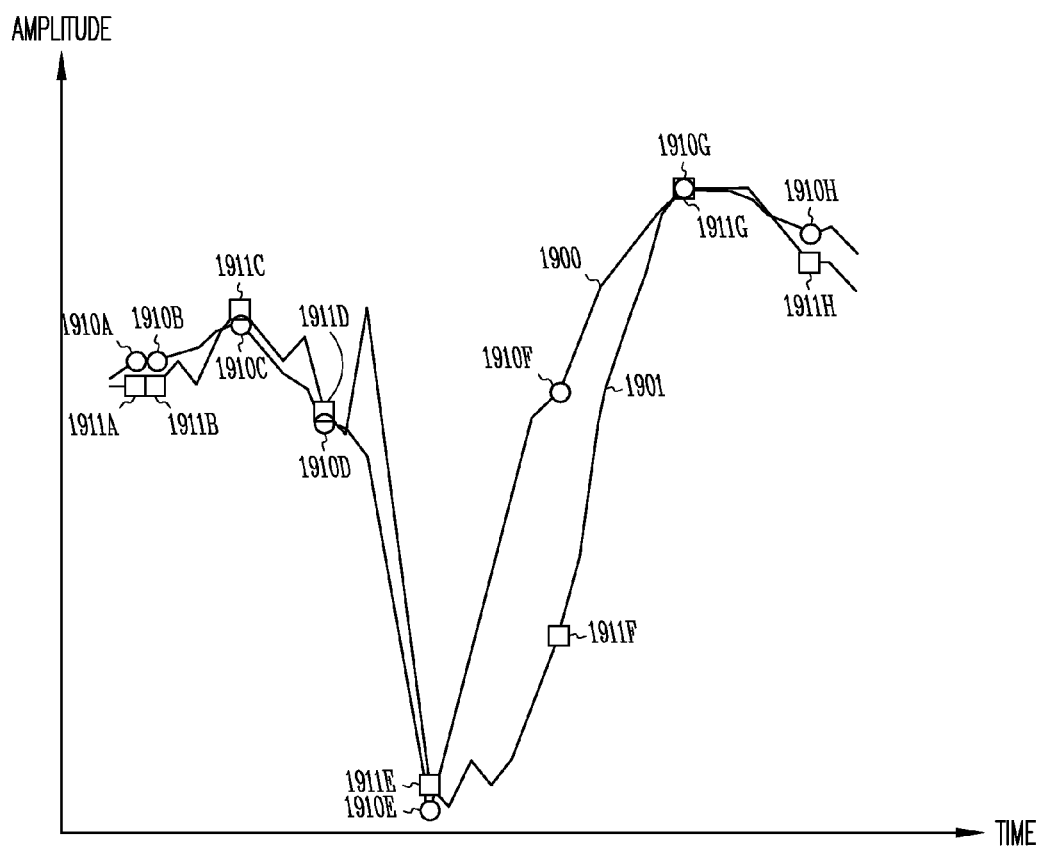
FIG. 19 is a graph illustrating exemplary template and arrhythmic waveforms used in the method of FIG. 18.

FIG. 19 is a graph illustrating exemplary template and arrhythmic waveforms showing an advantage of using method 1800. A template waveform 1900 is the template waveform being an averaged waveform representing the plurality of template heart beats of the known type cardiac rhythm. An arrhythmic waveform 1901 is the waveform of the arrhythmic heart beat sensed during the 1:1 tachyarrhythmia.

Template waveform 1900 includes template morphological features 1910A-H. Arrhythmic waveform 1901 includes arrhythmic morphological features 1911A-H, which are temporally corresponding to template morphological features 1910A-H. In the Mahalanobis distance-based correlation analysis, a template morphology feature associated with a relatively large variability among the plurality of template heart beats has a relatively smaller weight in the computation of the Mahalanobis distance-based correlation coefficient (mFcc). In the example of FIG. 19, template morphological feature 1910F has a relatively large variation among the plurality of template heart beats. Thus, even though arrhythmic morphological feature 1911F differs significantly from template morphological feature 1910F in terms of amplitude, the Mahalanobis distance-based correlation coefficient (mFcc) is 0.99. That is, the arrhythmic heart beat and the template heart beat as shown in FIG. 19 are substantially correlated. In one specific embodiment, as illustrated in FIG. 19, the template heart beat is a heart beat of an NSR, and the arrhythmic heart beat of the 1:1 tachyarrhythmia is discriminated between an SVT heart beat and a VT heart beat. The Mahalanobis distance-based correlation coefficient (mFcc) of 0.99 supports a classification of an SVT heart beat.

Figure 20:
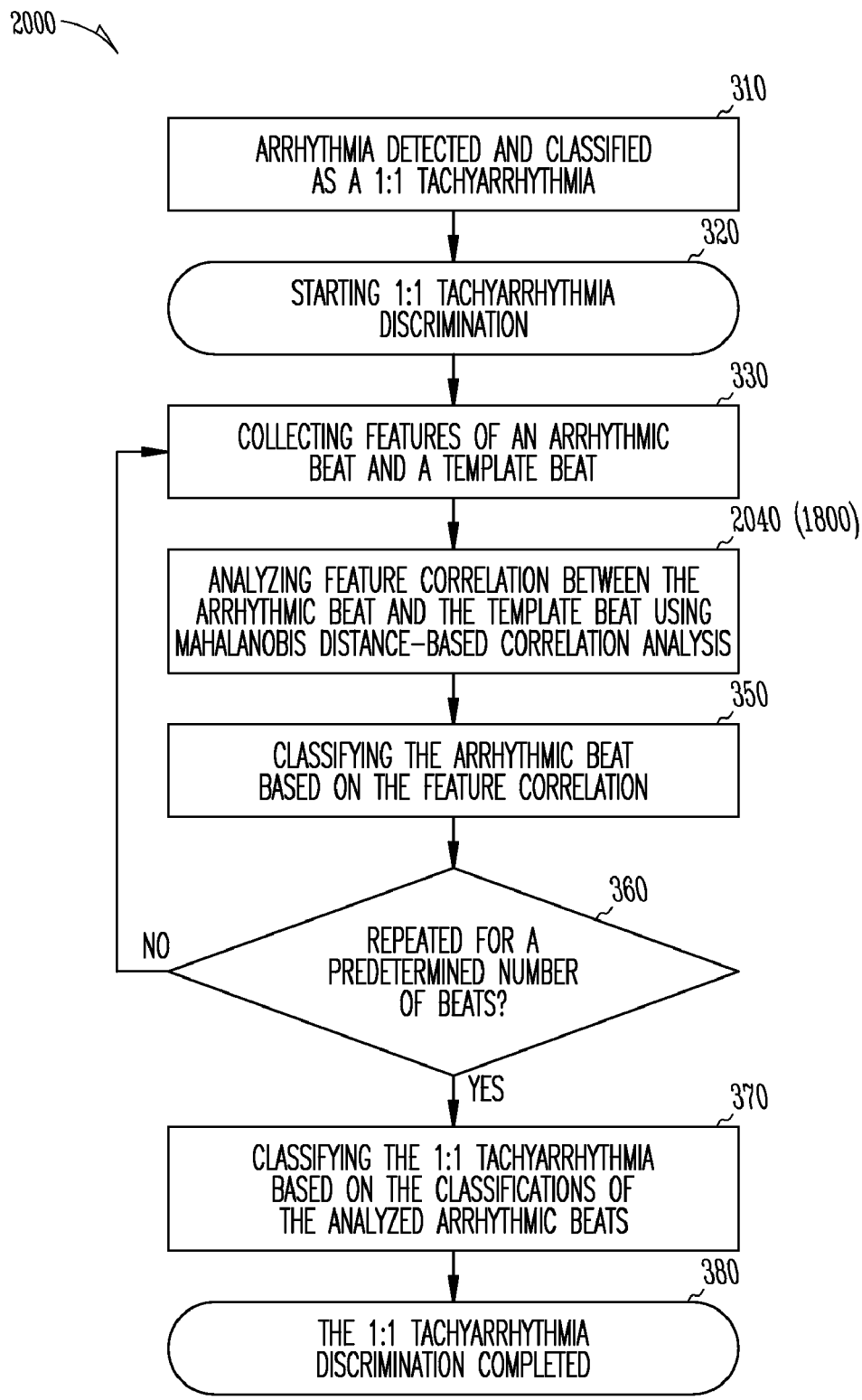
FIG. 20 is a flow chart illustrating a specific embodiment of the method for morphology-based 1:1 tachyarrhythmia discrimination as illustrated in FIG. 3 including an exemplary application of the method of FIG. 18.

FIG. 20 is a flow chart illustrating a method 2000 for the morphology-based tachyarrhythmia discrimination. Method 2000 is a specific embodiment of method 300 and includes an exemplary application of method 1800. Step 2040 in method 2000 is a specific embodiment of step 340 and includes method 1800 as discussed above.

The Mahalanobis distance-based correlation analysis takes into account the variability of and co-variability between morphological features. Instead of treating all template morphological features equally, the weight of each template morphological feature in the computation of the Mahalanobis distance-based correlation coefficient (mFcc) depends on the variability of that template morphological feature as measured from the plurality of template heart beats. The purpose is to prevent normal variations in the morphology of a heart beat from being detected as an indication of an arrhythmia of a particular type.

Morphological Stability Analysis

Figure 21:
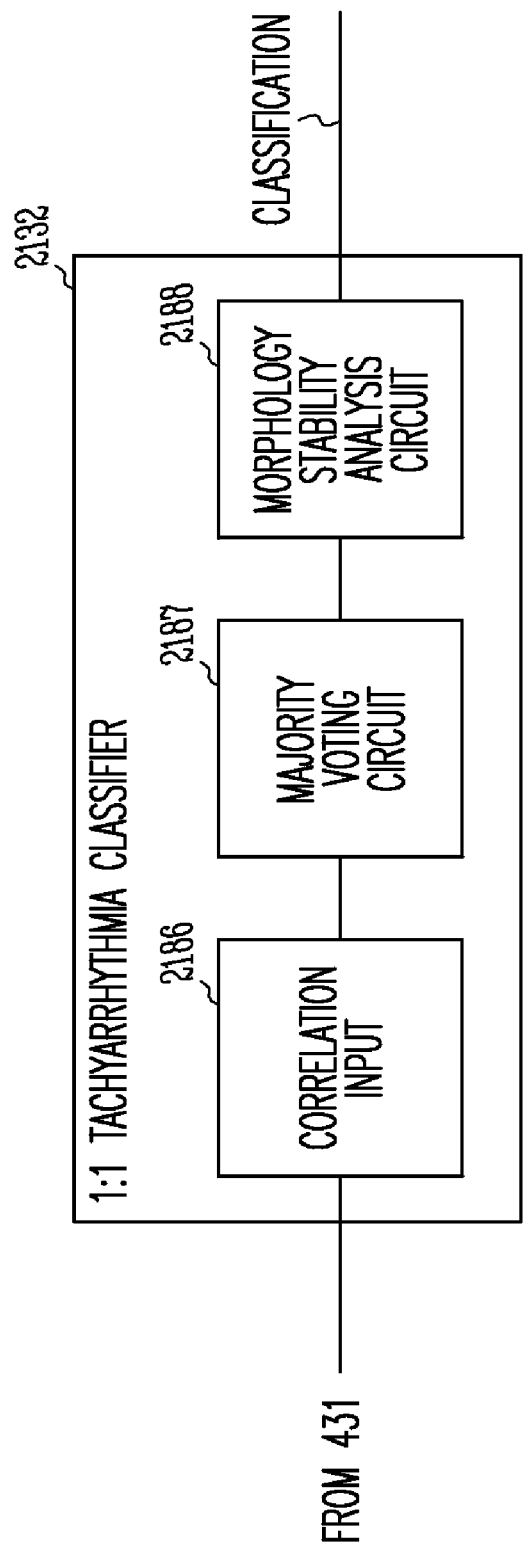
FIG. 21 is a block diagram illustrating an embodiment of another 1:1 tachyarrhythmia classifier being part of the morphology-based 1:1 tachyarrhythmia discrimination circuit.

FIG. 21 is a block diagram illustrating an embodiment of a 1:1 tachyarrhythmia classifier 2132. As a specific embodiment of 1:1 tachyarrhythmia classifier 432, 1:1 tachyarrhythmia classifier 2132 includes a correlation input 2186, a majority voting circuit 2187, and a morphology stability analysis circuit 2188.

Correlation input 2186 receives a plurality of feature correlation coefficient (Fcc) values each associated with an arrhythmic heart beat of a plurality of heart beats sensed during a 1:1 tachyarrhythmia. Each feature correlation coefficient (Fcc) value indicates whether the associated arrhythmic heart beat is morphologically correlated to a template heart beat of a known type cardiac rhythm. Majority voting circuit 2187 classifies the 1:1 tachyarrhythmia as a particular type tachyarrhythmia by a majority voting. That is, if the number of the arrhythmic heart beats that are correlated to the template heart beat equals or exceeds a predetermined threshold number, the 1:1 tachyarrhythmia is classified as that particular type tachyarrhythmia. If the number of the arrhythmic heart beats that are correlated to the template heart beat is smaller than the predetermined threshold number, morphology stability analysis circuit 2188 further classifies the 1:1 tachyarrhythmia based the stability of morphology as indicated by the feature correlation coefficient (Fcc) values.

Figure 22:
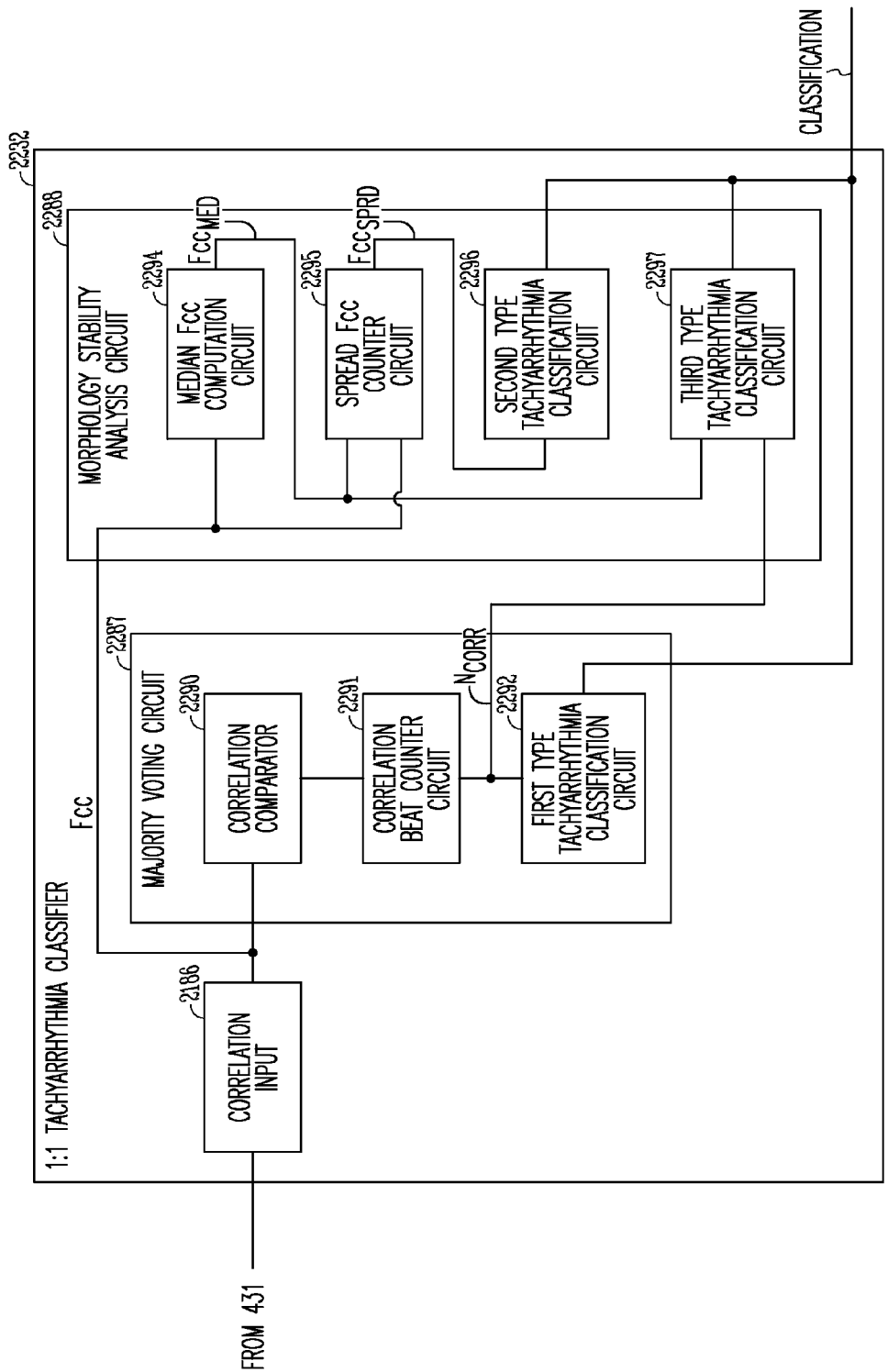
FIG. 22 is a block diagram illustrating a specific embodiment of the 1:1 tachyarrhythmia classifier of FIG. 21.

FIG. 22 is a block diagram illustrating an embodiment of a 1:1 tachyarrhythmia classifier 2232. As a specific embodiment of 1:1 tachyarrhythmia classifier 2132, 1:1 tachyarrhythmia classifier 2232 includes correlation input 2186, a majority voting circuit 2287, and a morphology stability analysis circuit 2288.

Majority voting circuit 2287 is a specific embodiment of majority voting circuit 2187 and includes a correlation comparator 2290, a correlated beat counter circuit 2291, and a first type tachyarrhythmia classification circuit 2292. Correlation comparator 2290 receives each feature correlation coefficient (Fcc) value from correlation input 2186 and compares the feature correlation coefficient (Fcc) value to a predetermined detection threshold ($Fcc_{th}$). If the feature correlation coefficient (Fcc) value is greater than the predetermined detection threshold ($Fcc_{th}$), correlation comparator 2290 indicates a correlated beat. Correlated beat counter circuit 2291 counts the number of the correlated beats ($N_{CORR}$) indicated by correlation comparator 2290. First type tachyarrhythmia classification circuit 2292 classifies the 1:1 tachyarrhythmia as the first type tachyarrhythmia if the number of the correlated beats ($N_{CORR}$) equals or exceeds a predetermined threshold number. That is, the 1:1 tachyarrhythmia is classified as the first type tachyarrhythmia if a minimum number of the arrhythmic heart beats out of the plurality of heart beats sensed during the 1:1 tachyarrhythmia equals or exceeds a threshold number defining the majority.

Morphology stability analysis circuit 2288 is a specific embodiment of morphology stability analysis circuit 2188 and includes a median Fcc computation circuit 2294, a spread Fcc counter circuit 2295, a second type tachyarrhythmia classification circuit 2296, and a third type tachyarrhythmia classification circuit 2297. Median Fcc computation circuit 2294 computes a median feature correlation coefficient ($Fcc_{MED}$) being a median value of the plurality of feature correlation coefficient (Fcc) values. Spread Fcc counter circuit 2295 counts a feature correlation coefficient spread number ($Fcc_{SPRD}$) being a number of feature correlation coefficient (Fcc) values of the plurality of feature correlation coefficient (Fcc) values that are within a window centered at the median feature correlation coefficient ($Fcc_{MED}$). Second type tachyarrhythmia classification circuit 2296 classifies the 1:1 tachyarrhythmia as a second type tachyarrhythmia based on the feature correlation coefficient spread number ($Fcc_{SPRD}$). If the 1:1 tachyarrhythmia is not classified as the second type tachyarrhythmia, third type tachyarrhythmia classification circuit 2297 classifies the 1:1 tachyarrhythmia as one of a third type tachyarrhythmia and the first type tachyarrhythmia based on the median feature correlation coefficient ($Fcc_{MED}$) and the number of the correlated beats ($N_{CORR}$).

In one embodiment, the template heart beat is a heart beat of an NSR. First type tachyarrhythmia classification circuit 2292 classifies the 1:1 tachyarrhythmia as an SVT if the number of the correlated beats ($N_{CORR}$) equals or exceeds the predetermined threshold number. If the feature correlation coefficient spread number ($Fcc_{SPRD}$) is smaller than a predetermined threshold spread number, second type tachyarrhythmia classification circuit 2296 classifies the 1:1 tachyarrhythmia as a polymorphic ventricular tachyarrhythmia (PVT). If the feature correlation coefficient spread number ($Fcc_{SPRD}$) is not smaller than the predetermined threshold spread number, the median feature correlation coefficient ($Fcc_{MED}$) is equal to or smaller than a predetermined threshold median, and the number of the correlated beats ($N_{CORR}$) is smaller than a predetermined threshold number, third type tachyarrhythmia classification circuit 2297 classifies the 1:1 tachyarrhythmia as a monomorphic ventricular tachyarrhythmia (MVT). If the feature correlation coefficient spread number ($Fcc_{SPRD}$) is not smaller than the predetermined threshold spread number, the median feature correlation coefficient ($Fcc_{MED}$) is greater than the predetermined threshold median, and the number of the correlated beats ($N_{CORR}$) is equal to or greater than the predetermined threshold number, third type tachyarrhythmia classification circuit 2297 classifies the 1:1 tachyarrhythmia as an SVT.

Figure 23:
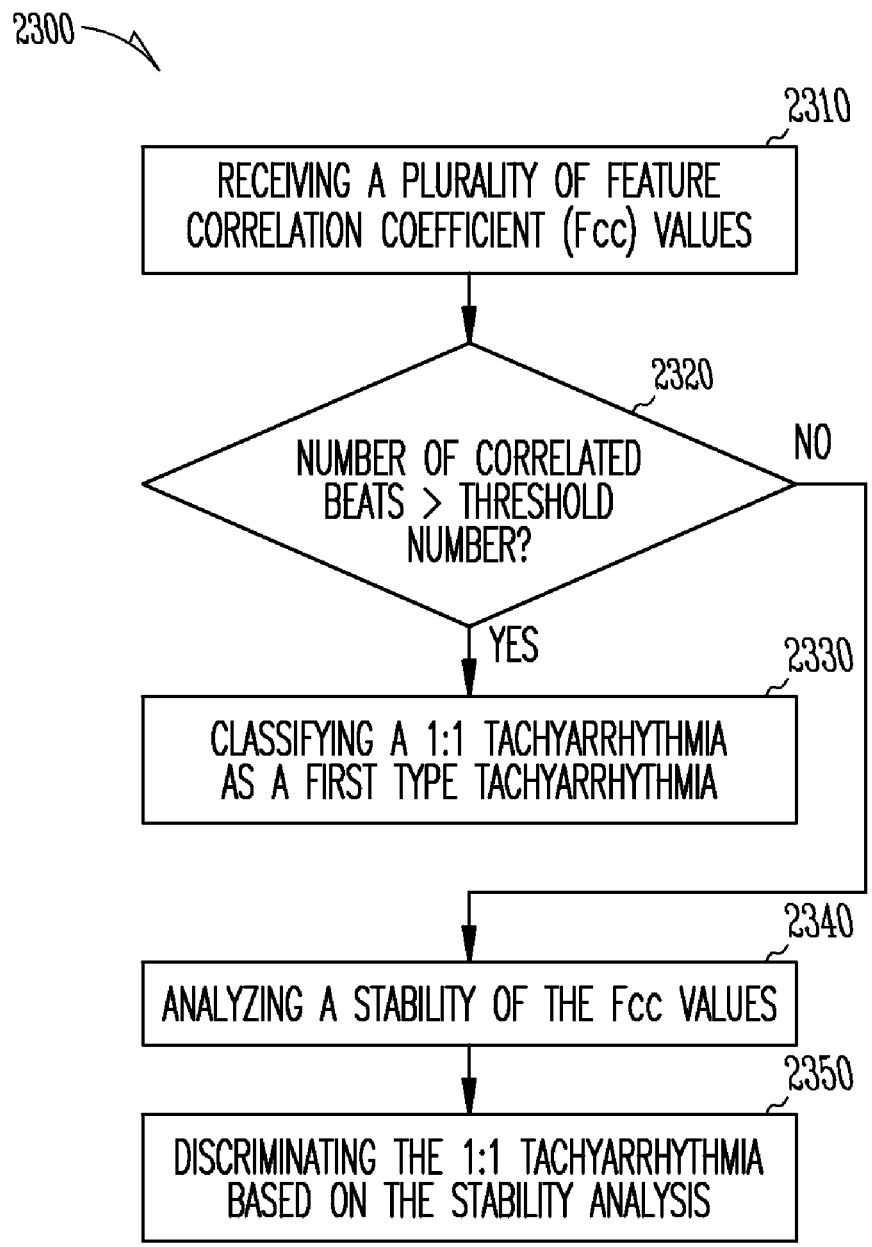
FIG. 23 is a flow chart illustrating an embodiment of another method for classifying 1:1 tachyarrhythmias for the morphology-based 1:1 tachyarrhythmia discrimination.

FIG. 23 is a flow chart illustrating an embodiment of a method 2300 for classifying a 1:1 tachyarrhythmia for the morphology-based 1:1 tachyarrhythmia discrimination. In one embodiment, method 2300 is performed by 1:1 tachyarrhythmia classifier 2132, including its specific embodiment, 1:1 tachyarrhythmia classifier 2232.

Figure 24:
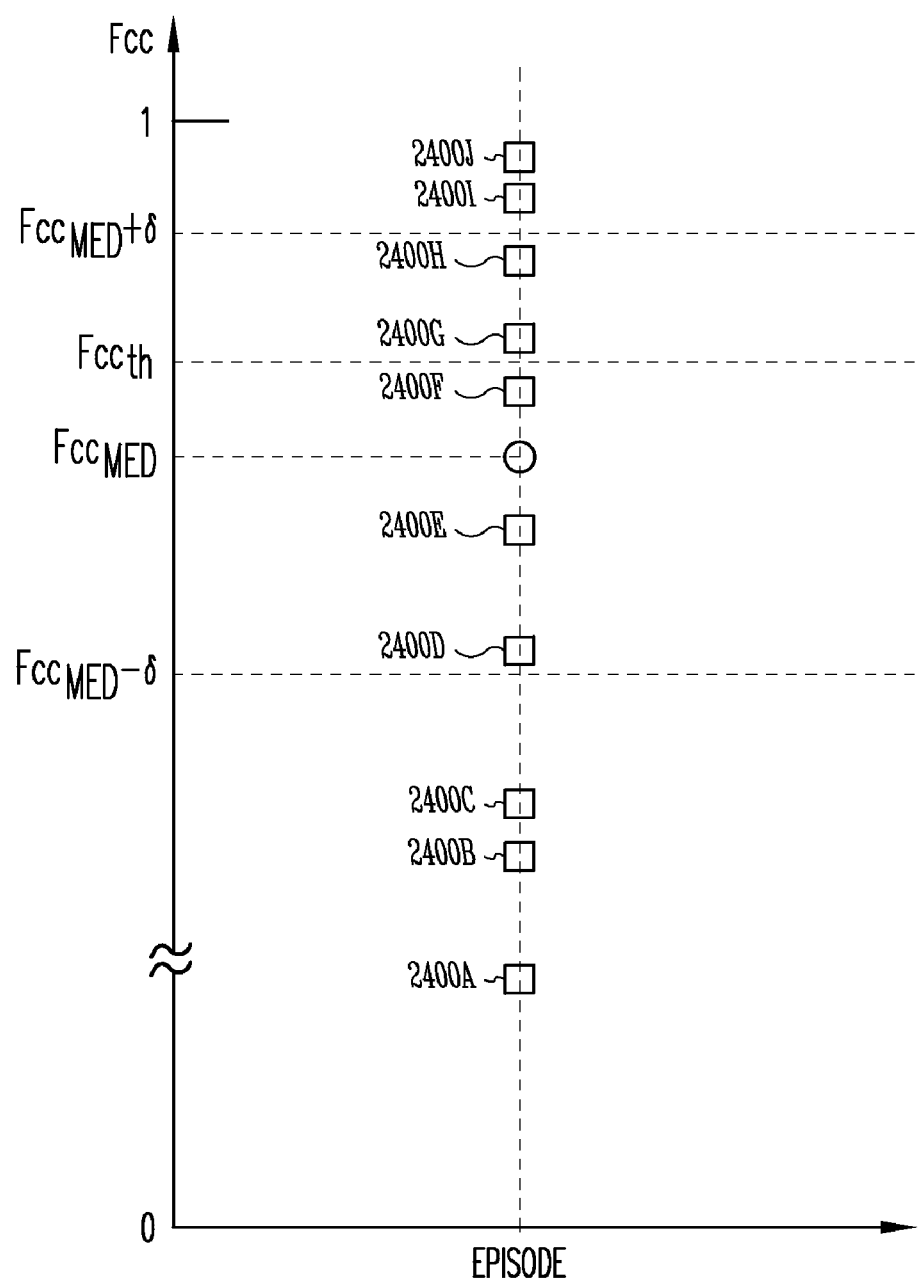
FIG. 24 is a graph illustrating exemplary distribution of correlation coefficients for an analysis using the method of FIG. 23.

A plurality of feature correlation coefficient (Fcc) values are received at 2310. An exemplary distribution of such feature correlation coefficient (Fcc) values are illustrated in FIG. 24. The plurality of feature correlation coefficient (Fcc) values are associated with a plurality of arrhythmic heart beats sensed during a detected 1:1 tachyarrhythmia. Each feature correlation coefficient (Fcc) value indicates whether an arrhythmic heart beat is morphologically correlated to a template heart beat of a known type cardiac rhythm. The number of arrhythmic heart beats that are correlated to the template heart beat ($N_{CORR}$), i.e., the number of the arrhythmic heart beats associated with an feature correlation coefficient (Fcc) value that exceeds a predetermined threshold Fcc value ($Fcc_{th}$), is counted. If the number of the correlated beats ($N_{CORR}$) equals or exceeds a predetermined threshold number ($Fcc_{th}$) at 2320, the 1:1 tachyarrhythmia is classified as a first type tachyarrhythmia at 2330. If the number of the correlated beats ($N_{CORR}$) is smaller than the predetermined threshold number, the stability of the feature correlation coefficient (Fcc) values are analyzed at 2340, and the 1:1 tachyarrhythmia is classified based on the stability analysis at 2350.

The stability analysis looks into the distribution of the feature correlation coefficient (Fcc) values for the plurality of arrhythmic heart beats. A median feature correlation coefficient ($Fcc_{MED}$) is calculated as the median value of the feature correlation coefficient (Fcc) values. An feature correlation coefficient spread number ($Fcc_{SPRD}$) is counted to indicate the number of feature correlation coefficient (Fcc) values that are within a window centered at the median feature correlation coefficient ($Fcc_{MED}$). The 1:1 tachyarrhythmia is classified as a second type tachyarrhythmia based on the feature correlation coefficient spread number ($Fcc_{SPRD}$). If the 1:1 tachyarrhythmia is not classified as the second type tachyarrhythmia, it is classified as one of a third type tachyarrhythmia and the first type tachyarrhythmia based on the feature correlation coefficient spread and the number of the correlated beats ($N_{CORR}$). In one embodiment, the template heart beat represents a heart beat of an NSR, the first type tachyarrhythmia is SVT, the second type tachyarrhythmia is PVT, and the third type tachyarrhythmia is MVT. The 1:1 tachyarrhythmia is classified as a PVT if the feature correlation coefficient spread number ($Fcc_{SPRD}$) is smaller than a predetermined threshold spread number. If the feature correlation coefficient spread number ($Fcc_{SPRD}$) is not smaller than the predetermined threshold spread number, the 1:1 tachyarrhythmia is classified as an MVT if the median feature correlation coefficient ($Fcc_{MED}$) is equal to or smaller than a predetermined threshold median and the number of the correlated beats ($N_{CORR}$) is smaller than the predetermined threshold number, or as an SVT if the median feature correlation coefficient ($Fcc_{MED}$) is greater than the predetermined threshold median and the number of the correlated beats ($N_{CORR}$) is equal to or greater than the predetermined threshold number.

FIG. 24 is a graph illustrating an exemplary distribution of feature correlation coefficient (Fcc) values 2400A-J for a plurality of arrhythmic heart beats sensed during an episode of the 1:1 tachyarrhythmia. The distribution of feature correlation coefficient (Fcc) values each associated with one of ten arrhythmic heart beats are shown. Four out of the ten feature correlation coefficient (Fcc) values are above the predetermined detection threshold ($Fcc_{th}$). That is, the number of the correlated beats ($N_{CORR}$) is equal to four. Because the number of the correlated beats ($N_{CORR}$) is smaller than the threshold number (that defines majority) needed to classify the 1:1 tachyarrhythmia as the first type tachyarrhythmia, a stability analysis for the feature correlation coefficient (Fcc) values is performed. This includes a calculation of the median feature correlation coefficient ($Fcc_{MED}$) and a counting of the feature correlation coefficient spread number ($Fcc_{SPRD}$). The feature correlation coefficient spread number ($Fcc_{SPRD}$) is the number of Fcc values that fall into a window defined by $Fcc_{MED} \pm \delta$ ($Fcc_{SPRD}=5$ as illustrated in FIG. 24). Parameters including $\delta$, the predetermined detection threshold ($Fcc_{th}$), the predetermined threshold median, and the predetermined threshold number are empirically determined. The number of the correlated beats ($N_{CORR}$), the median feature correlation coefficient ($Fcc_{MED}$), and the feature correlation coefficient spread number ($Fcc_{SPRD}$), show the stability of the feature correlation coefficient (Fcc) values as measured by their distribution.

Figure 25:
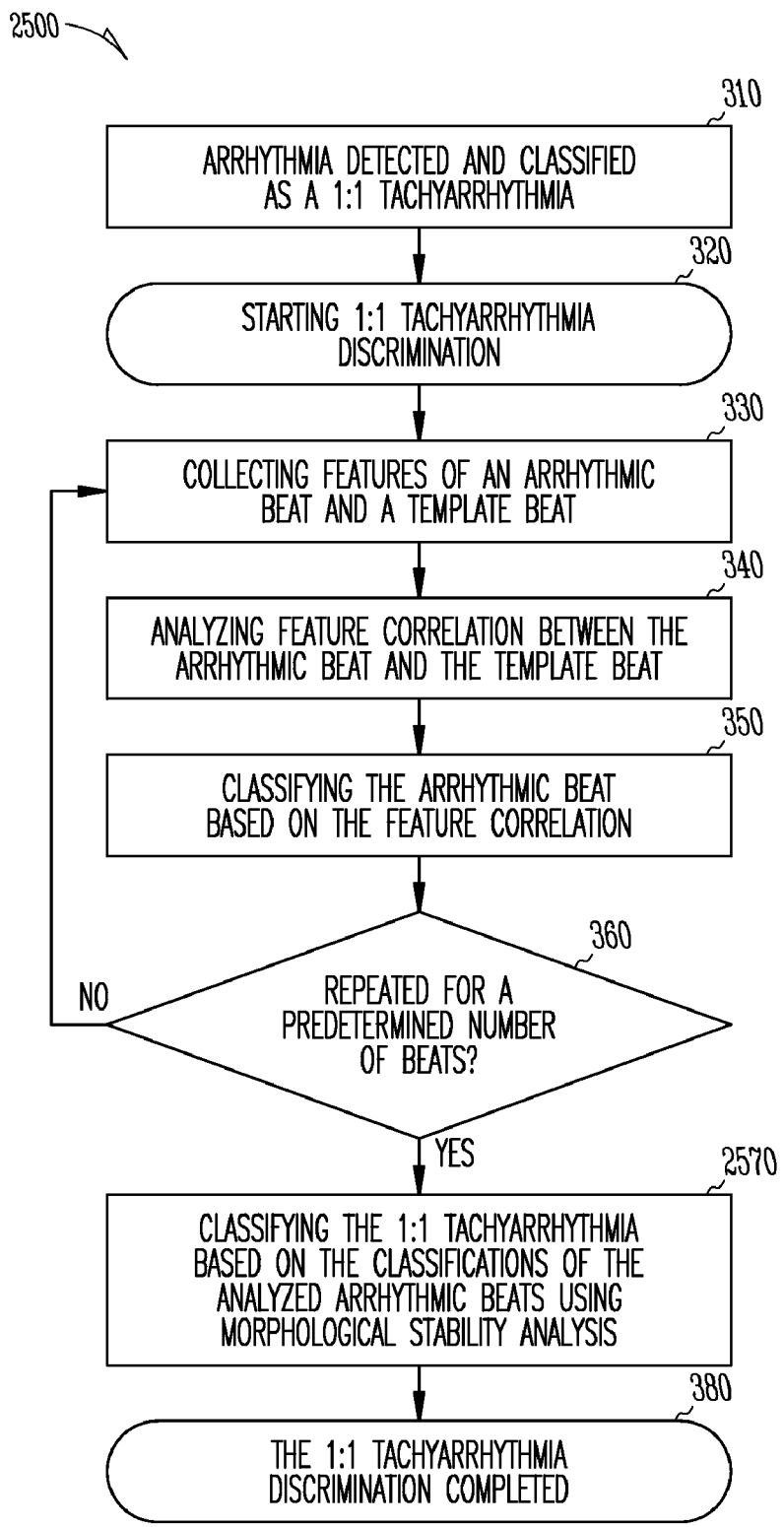
FIG. 25 is a flow chart illustrating a specific embodiment of the method for morphology-based 1:1 tachyarrhythmia discrimination as illustrated in FIG. 3 including an exemplary application of the method of FIG. 23.

FIG. 25 is a flow chart illustrating a method 2500 for the morphology-based tachyarrhythmia discrimination. Method 2500 is a specific embodiment of method 300 and includes an exemplary application of method 2300. Step 2570 in method 2500 is a specific embodiment of step 370 and includes method 2300 as discussed above.

While a known, simpler method classifies an 1:1 tachyarrhythmia as one of SVT and VT by a majority voting based on the feature correlation coefficient (Fcc) values, method 2500 provides for further discrimination between PVT and MVT as well as identification of "borderline" SVTs. This further eliminates unnecessary deliveries of ventricular defibrillation shocks. In one embodiment, a PVT is immediately treated with one or more ventricular defibrillation shocks, while anti-tachycardia pacing (ATP) is delivered during on or more attempts to terminate an MVT. Thus, when the majority voting does not result in a classification of SVT, the stability analysis provides further bases for eliminating unnecessary ventricular defibrillation shocks that cause significant discomfort to the patient and shortens the life expectancy of an ICD.

In General

Classification of a 1:1 tachyarrhythmia can be performed using variations of the embodiments and/or various combinations of the embodiments discussed above without deviating from the concepts embedded in these embodiments. In one exemplary combination, a system performing method 300 includes a sub-system for performing method 700 as step 330 and another sub-system for performing method 2300 as step 370. In another exemplary combination, a system performing method 300 may include a sub-system for performing method 1800 as step 340 and another sub-system for performing method 2300 as step 370. In another exemplary combination, a system performing method 300 includes a first sub-system for performing method 700 as step 330, a second sub-system for performing method 1200 as step 340, and a third sub-system for performing method 2300 as step 370. Other possible combination of the embodiments discussed above will be apparent to those skilled in the art, upon reading and comprehending this document.

The relationship between a rate and an interval, as used in this document, is the relationship between a frequency and its corresponding period. If a rate is given in beats per minute (bpm), its corresponding interval in millisecond is calculated by dividing 60,000 by the rate (where 60,000 is the number of milliseconds in a minute). Any process, such as a comparison, using the rates is to be modified accordingly when the intervals are used instead. For example, if a tachyarrhythmia is detected when the ventricular rate exceeds a tachyarrhythmia threshold rate, an equivalent process is to detect the tachyarrhythmia when the ventricular interval falls below a tachyarrhythmia threshold interval. The appended claims should be construed to cover such variations. For example, atrial and ventricular intervals should be construed as equivalent to the atrial and ventricular rates, respectively.

It is to be understood that the above detailed description is intended to be illustrative, and not restrictive. For example, system 120, circuit 225, and their various embodiments as discussed in this document are not limited to applications in an ICD, but may be incorporated into any arrhythmia analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for classifying tachyarrhythmias, the system comprising:
   a feature vector generation circuit configured to produce a template feature vector (a) using a plurality of template morphological features on a plurality of template waveforms each associated with a template heart beat of a known type cardiac rhythm, an arrhythmic feature vector (b) using a plurality of arrhythmic morphological features of an arrhythmic waveform associated with an arrhythmic heart beat sensed during a tachyarrhythmia, and a maximum feature vector ($a_{max}$) and a minimum feature vector ($a_{min}$) using the plurality of template morphological features, the plurality of arrhythmic morphological features, the maximum feature vector ($a_{max}$) and the minimum feature vector ($a_{min}$) being within a template band associated with predetermined confidence levels of the plurality of template morphological features;
   a correlation computing circuit coupled to the feature vector generation circuit, the correlation computing circuit configured to calculate a mean feature correlation coefficient ($Fcc_{mean}$) using the template feature vector (a) and the arrhythmic feature vector (b), a maximum feature correlation coefficient ($Fcc_{max}$) using the maximum feature vector ($a_{max}$) and the arrhythmic feature vector (b), and a minimum feature correlation coefficient ($Fcc_{min}$) using the minimum feature vector ($a_{min}$) and the arrhythmic feature vector (b); and
   a beat classification circuit coupled to the correlation analysis circuit, the beat classification circuit configured to classify the arrhythmic heart beat using the mean feature correlation coefficient ($Fcc_{mean}$), the maximum feature correlation coefficient ($Fcc_{max}$), the minimum feature correlation coefficient ($Fcc_{min}$), and at least one predetermined correlation threshold.

2. The system of claim 1, wherein the beat classification circuit comprises a decision circuit configured to calculate a score for the arrhythmic heart beat using the mean feature correlation coefficient ($Fcc_{mean}$), the maximum feature correlation coefficient ($Fcc_{max}$) the minimum feature correlation coefficient ($Fcc_{min}$), and the predetermined correlation threshold, the score indicative of a probability of the tachyarrhythmia being a first type tachyarrhythmia.

3. The system of claim 2, comprising an episode classification circuit coupled to the beat classification circuit, the episode classification circuit configured to classify the tachyarrhythmia using the scores produced for a plurality of arrhythmic heart beats sensed during the tachyarrhythmia.

4. The system of claim 3, wherein the episode classification circuit comprises:
   a score averaging circuit configured to calculate an episode score being an average of the scores produced for the plurality of arrhythmic heart beats, and
   a comparator configured to compare the episode score to a predetermined classification threshold and classify the tachyarrhythmia as the first type tachyarrhythmia in response to the episode score exceeding the predetermined classification threshold.

5. The system of claim 1, wherein feature vector generation circuit comprises:
   a template band construction circuit to produce the template feature vector (a) and a template standard deviation vector ($\sigma$) using the plurality of template morphological features;
   an arrhythmic feature vector generation circuit configured to produce the arrhythmic feature vector (b) using the plurality of arrhythmic morphological features;
   a deviation vector generation circuit configured to produce a maximum deviation vector ($x_{max}$) and a minimum deviation vector ($x_{min}$) based on at least the template feature (a) vector, the arrhythmic feature vector (b), and the template standard deviation vector ($\sigma$), the maximum deviation vector ($x_{max}$) and the minimum deviation vector ($x_{min}$) indicative of morphological variations among the plurality of template morphological features; and
   a boundary feature vector generation circuit configured to produce the maximum feature vector ($a_{max}$) by adding the maximum deviation vector ($x_{max}$) to the template feature vector (a) and produce the minimum feature vector ($a_{min}$) by adding the minimum deviation vector ($x_{min}$) to the template feature vector (a).

6. The system of claim 5, wherein the template band construction circuit comprises:
   a template vector generator configured to produce a plurality of template feature vectors each associated with one template heart beat of the plurality of template heart beats;
   a mean vector calculator configured to produce the template feature vector (a) being a mean vector of the plurality of template feature vectors; and
   a standard deviation vector calculator configured to produce the template standard deviation vector ($\sigma$) being a standard deviation vector of the plurality of template feature vectors.

7. The system of claim 1, comprising an implantable cardiovertor/defibrillator (ICD) including the feature vector generation circuit, the correlation computing circuit, and the beat classification circuit.

8. The system of claim 7, wherein the ICD comprises:
   a sensing circuit configured to sense an atrial electrogram and a ventricular electrogram;
   a rate detection circuit configured to detect to an atrial rate using the atrial electrogram and a ventricular rate using the ventricular electrogram; and a tachyarrhythmia detection circuit configured to detect the tachyarrhythmia using at least one of the atrial rate and the ventricular rate.

9. The system of claim 8, wherein the ICD comprises a rhythm classification circuit configured to classify the detected tachyarrhythmia as a 1:1 tachyarrhythmia in response to a determination that the atrial rate and the ventricular rate are substantially equal during the detected tachyarrhythmia, and wherein the feature vector generation circuit is adapted to produce the arrhythmic feature vector (b) based on a plurality of arrhythmic morphological features of an arrhythmic waveform associated with an arrhythmic heart beat sensed during the detected tachyarrhythmia classified as the 1:1 tachyarrhythmia.

10. A method for classifying tachyarrhythmias, the method comprising:
producing a template feature vector (a) and a template standard deviation vector ($\sigma$) based on template morphological features on a plurality of template waveforms each associated with a heart beat of a known type cardiac rhythm;
producing an arrhythmic feature vector (b) based on arrhythmia morphological features on an arrhythmic waveform associated with an arrhythmic heart beat sensed during a tachyarrhythmia;
producing a maximum deviation vector ($x_{max}$) and a minimum deviation vector ($x_{min}$) based on at least the template feature vector (a), the arrhythmic feature vector (b), and the template standard deviation vector ($\sigma$), the maximum deviation vector ($x_{max}$) and the minimum deviation vector ($x_{min}$) indicative of morphological variations among the plurality of template morphological features;
producing a maximum feature vector ($a_{max}$) by adding the maximum deviation vector ($x_{max}$) to the template feature vector (a) and a minimum feature vector ($a_{min}$) by adding the minimum deviation vector ($x_{min}$) to the template feature vector (a); computing a mean feature correlation coefficient ($Fcc_{mean}$) based on the template feature vector (a) and the arrhythmic feature vector (b), a maximum feature correlation coefficient ($Fcc_{max}$) based on the maximum feature vector ($a_{max}$) and the arrhythmic feature vector (b), and a minimum feature correlation coefficient ($Fcc_{min}$) based on the minimum feature vector ($a_{min}$) and the arrhythmic feature vector (b); and
classifying the arrhythmic heart beat based on the mean feature correlation coefficient ($Fcc_{mean}$), the maximum feature correlation coefficient ($Fcc_{max}$), the minimum feature correlation coefficient ($Fcc_{min}$), and at least one predetermined correlation threshold.

11. The method of claim 10, wherein classifying the arrhythmic heart beat comprises computing a score for the arrhythmic heart beat based on the mean feature correlation coefficient ($Fcc_{mean}$), the maximum feature correlation coefficient ($Fcc_{max}$), the minimum feature correlation coefficient ($Fcc_{min}$), and a predetermined correlation threshold, the score indicative of a probability of the tachyarrhythmia being the first type tachyarrhythmia.

12. The method of claim 11, wherein classifying the arrhythmic heart beat further comprises:
setting the score to 1 if the maximum feature correlation coefficient ($Fcc_{max}$) is below the predetermined correlation threshold; and
setting the score to 0 if the minimum feature correlation coefficient ($Fcc_{min}$) exceeds the predetermined correlation threshold.

13. The method of claim 11, further comprising classifying the tachyarrhythmia based on the scores produced for a plurality of arrhythmic heart beats of the tachyarrhythmia.

14. The method of claim 13, wherein classifying the tachyarrhythmia comprises:
calculating an episode score being an average of the scores produced for the plurality of arrhythmic heart beats;
comparing the episode score to a predetermined classification threshold; and
classifying the tachyarrhythmia as the first type tachyarrhythmia if the episode score exceeds the predetermined classification threshold.

15. The method of claim 14, wherein the known rhythm is a normal sinus rhythm, and the first type tachyarrhythmia is a supraventricular tachyarrhythmia.

16. The method of claim 10, wherein producing the template feature vector (a) and a template standard deviation vector ($\sigma$) comprises:
receiving a plurality of feature vectors each associated with one template waveform of the plurality of template waveforms;
producing the template feature vector (a) being a mean vector of the plurality of feature vectors; and
producing the template standard deviation vector ($\sigma$) being a standard deviation vector of the plurality of feature vectors.

17. The method of claim 16, wherein producing the arrhythmic feature vector (b) comprises:
receiving the arrhythmic waveform;
extracting the morphological features from the arrhythmic waveform; and
producing the arrhythmic feature vector (based on the plurality of morphological features.

18. The method of claim 10, comprising:
sensing an atrial electrogram and a ventricular electrogram;
detecting an atrial rate using the atrial electrogram;
detecting a ventricular rate using the ventricular electrogram; and
detecting the tachyarrhythmia using at least one of the atrial rate and the ventricular rate.

19. The method of claim 18, wherein the tachyarrhythmia is a 1:1 tachyarrhythmia, and comprising classifying the detected tachyarrhythmia as a 1:1 tachyarrhythmia when the atrial rate and the ventricular rate are substantially equal.

20. A system for classifying tachyarrhythmias, the system comprising:
means for producing a template feature vector (a) and a template standard deviation vector ($\sigma$) based on template morphological features on a plurality of template waveforms each associated with a heart beat of a known type cardiac rhythm;
means for producing an arrhythmic feature vector (b) based on arrhythmia morphological features on an arrhythmic waveform associated with an arrhythmic heart beat sensed during a tachyarrhythmia;
means for producing a maximum deviation vector ($x_{max}$) and a minimum deviation vector ($x_{min}$) based on at least the template feature vector (a), the arrhythmic feature vector (b), and the template standard deviation vector ($\sigma$), the maximum deviation vector ($x_{max}$) and the minimum deviation vector ($x_{min}$) indicative of morphological variations among the plurality of template morphological features;
means for producing a maximum feature vector ($a_{max}$) by adding the maximum deviation vector ($x_{max}$) to the template feature vector (a) and a minimum feature vector ($a_{min}$) by adding the minimum deviation vector ($x_{min}$) to the template feature vector (a), computing a mean feature correlation coefficient ($Fcc_{mean}$) based on the template feature vector ($\underline{a}$) and the arrhythmic feature vector ($\underline{b}$), a maximum feature correlation coefficient ($Fcc_{max}$) based on the maximum feature vector ($\underline{a}_{max}$) and the arrhythmic feature vector ($\underline{b}$), and a minimum feature correlation coefficient ($Fcc_{min}$) based on the minimum feature vector ($\underline{a}_{min}$) and the arrhythmic feature vector ($\underline{b}$); and means for classifying the arrhythmic heart beat based on the mean feature correlation coefficient ($Fcc_{mean}$), the maximum feature correlation coefficient ($Fcc_{max}$), the minimum feature correlation coefficient ($Fcc_{min}$), and at least one predetermined correlation threshold.

\* \* \* \* \*